(12) United States Patent
Wagner et al.

(10) Patent No.: US 7,781,438 B2
(45) Date of Patent: Aug. 24, 2010

(54) INDOLYLMALEIMIDE DERIVATIVES

(75) Inventors: Jürgen Wagner, Bottmingen (CH);
Maurice Van Eis, St. Louis (FR); Peter Von Matt, Biel-Benken BL (CH);
Jean-Pierre Evenou, St. Louis (FR);
Walter Schuler, Grenzach-Wyhlen (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 11/995,450

(22) PCT Filed: Jul. 10, 2006

(86) PCT No.: PCT/EP2006/006732

§ 371 (c)(1),
(2), (4) Date: Aug. 5, 2008

(87) PCT Pub. No.: WO2007/006533

PCT Pub. Date: Jan. 18, 2007

(65) Prior Publication Data

US 2008/0318975 A1    Dec. 25, 2008

(30) Foreign Application Priority Data

Jul. 11, 2005 (GB) ................. 0514204.7
Jul. 11, 2005 (GB) ................. 0514205.4

(51) Int. Cl.
*A61K 31/4965* (2006.01)
*A61K 31/40* (2006.01)
*A01N 43/52* (2006.01)
*A01N 43/56* (2006.01)
*C07D 401/00* (2006.01)

(52) U.S. Cl. ................. 514/255.05; 514/414; 514/394; 514/406; 514/314; 548/466; 548/306.1; 546/167

(58) Field of Classification Search ............ 514/255.05, 514/414, 394, 406, 314; 548/466, 306.1; 546/167

See application file for complete search history.

(56) References Cited

U.S. PATENT DOCUMENTS 36,736 A * 10/1862 Davis ..................... 119/631
5,057,614 A   10/1991 Davis et al.

FOREIGN PATENT DOCUMENTS

| EP | 0540956 B1 | 5/1993 |
| WO | WO02/38561 A1 | 5/2002 |
| WO | 03076398 * | 9/2003 |
| WO | WO03/082859 A1 | 10/2003 |
| WO | WO03/103663 A2 | 12/2003 |
| WO | WO03/104222 A1 | 12/2003 |
| WO | WO2005/068454 A1 | 7/2005 |
| WO | WO2005/068455 A1 | 7/2005 |

OTHER PUBLICATIONS

Davis et al., "Inhibitors of Protein Kinase C. 1.'2,3-Bisarylmaleimides", Journal of Medicinal Chemistry, 1992 vol. 35 pp. 177-184.
Hendricks et al., "2-Aryl-Indolyl Maleimides—Novel and Potent Inhibitors of Protein K1nase C", Bioorganic & Medicinal Chemistry Letters, 1995 vol. 5 No. 1 pp. 67-72.
Sanchez-Martinez et al., "Synthesis of Aryl- and Heteroaryl[a]pyrrolo[3,4-c]carbazoles", Journal of Organic Chemistry, 2003 vol. 68 pp. 8008-8014.
Zhu et al., "Synthesis of Quinolinyl/Isoquinolinyl[a]pyrrolo [3,4-c] Carbazoles as Cyclin D1/CDK4 Inhibitors", Bioorganic & Medicinal Chemistry Letters, 2003 vol. 13 pp. 1231-1235.

* cited by examiner

*Primary Examiner*—D. Margaret Seaman
*Assistant Examiner*—Niloofar Rahmani
(74) *Attorney, Agent, or Firm*—Hoxie & Associates LLC

(57) ABSTRACT

A compound of formula (I)

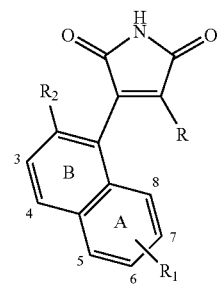

wherein R, $R_1$, and $R_2$, ring A and ring B are as defined in the specification, processes for their production, their uses, in particular in transplantation, and pharmaceutical compositions containing them.

9 Claims, No Drawings

INDOLYLMALEIMIDE DERIVATIVES

This application is a US National Phase filing of PCT/EP2006/006732 filed Jul. 10, 2006, and claims priority to GB Patent Application Serial No. 0514204.7 filed Jul. 11, 2005 and GB Patent Application Serial No. 0514205.4 filed Jul. 11, 2005, the contents of which are incorporated herein by reference.

The present invention relates to new maleimide derivatives, processes for their production and pharmaceutical compositions containing them.

More particularly the present invention provides a compound of formula (I)

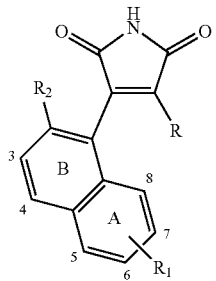

(I)

wherein
$R_1$ is a radical —$(CH_2)_n$—$NR_3R_4$, located on positions 6, 7 or 8,
wherein
n is 0, 1 or 2; and
each of $R_3$ and $R_4$, independently, is
hydrogen; $C_{1-6}$-alkyl; $C_{1-6}$alkyl substituted by OH, halogen, $NH_2$, $NHC_{1-4}$alkyl, $N(di-C_{1-4}alkyl)_2$, $C_{1-6}$alkoxy, or $C_{3-6}$cycloalkyl; $C_{3-6}$cycloalkyl; carboxy-$C_{1-6}$alkoxy; $C_{1-6}$alkoxy-carbonyl; $C_{2-4}$alkenyl; or $C_{1-6}$alkyl-carbonyl;
or $R_3$ and $R_4$ form together with the nitrogen atom to which they are bound a heterocyclic residue;
$R_2$ is hydrogen; halogen; $CF_3$; OH; CN; SH; $NH_2$; $NO_2$; —CHO; $C(O)NH_2$; optionally substituted $C_{1-4}$alkyl; $C_{1-4}$alkylthio; $C_{1-4}$alkoxy; $C_{1-4}$alkyl-sulfoxide; $C_{1-4}$alkyl-sulfone; $NHC_{1-4}$alkyl; $N(di-C_{1-4}alkyl)_2$; $C_{2-4}$alkenyl; $C_{1-4}$alkyl-carbamoyl; or $di(C_{1-4}alkyl)_2$-carbamoyl;
ring A may contain one or two nitrogen atoms;
ring B may further be substituted by halogen on position 4;
R is a radical of formula (a), (b), (c) or (d),

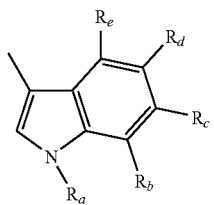

(a)

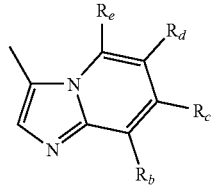

(b)

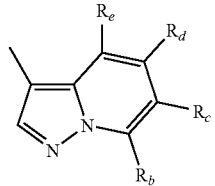

(c)

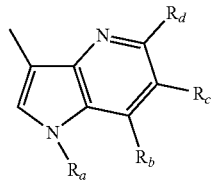

(d)

wherein
$R_a$ is hydrogen; $C_{1-6}$alkyl; $C_{1-6}$alkyl substituted by OH, $NH_2$, $NHC_{1-4}$alkyl, $N(di-C_{1-4}alkyl)_2$, heterocyclic group or $C_{1-12}$alkoxy optionally interrupted by one oxygen atom and optionally substituted by OH or $NH_2$; $C_{4-8}$cycloalkyl; optionally substituted heterocyclic group; and
either each of $R_b$, $R_c$ and $R_d$, independently, is
hydrogen; halogen; $CF_3$; CN; $C_{1-6}$alkyl; $C_{1-6}$-alkyl substituted by OH, $NH_2$, $NHC_{1-4}$alkyl, $N(di-C_{1-4}alkyl)_2$ or by $C_{1-12}$alkoxy optionally interrupted by one or two oxygen atom(s); $C_{1-15}$alkoxy optionally interrupted by one or two oxygen atom(s) and optionally substituted by halogen, OH, $NH_2$, or optionally substituted heterocyclic group; carbamoyl-$C_{1-6}$alkoxy; mono($C_{1-4}$alkyl)carbamoyl-$C_{1-6}$alkoxy; $di(C_{1-4}alkyl)_2$-carbamoyl-$C_{1-6}$alkoxy (19); carboxy-$C_{1-6}$alkoxy; or $C_{1-6}$alkoxy-carbonyl; or
of formula O—$(CH_2)_p$—$NR_vR_w$, wherein
each of $R_v$ and $R_w$, independently, is hydrogen or $C_{1-4}$alkyl; and
p is 2, 3 or 4; or
of formula —$(CH_2)_o$—$NR_vR_w$ wherein
each of $R_v$ and $R_w$, independently, is hydrogen; $C_{1-4}$alkyl$C_{1-6}$alkoxy (32); $C_{1-4}$alkyl-NH—$C_{1-4}$alkyl; or $C_{1-4}$alkyl-$N(di-C_{1-4}alkyl)_2$ (33) and
o is 1, 2, 3 or 4;
and $R_e$ is hydrogen; halogen; $CF_3$; CN; $C_{1-6}$-alkyl; or $C_{1-6}$alkoxy;
or $R_b$ and $R_c$ form together with the carbon atoms to which they are attached a $C_{5-8}$-carbocyclic group, and each of $R_d$ and $R_e$, independently, is hydrogen; halogen; $C_{1-4}$alkyl; or $C_{1-6}$alkoxy;

or $R_a$ and $R_b$ form together with the

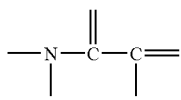

chain to which they are attached a heterocyclic group comprising at least one nitrogen atom and which is optionally substituted e.g. which heterocyclic group, and each of $R_c$, $R_d$ and $R_e$, independently, is hydrogen; halogen; $C_{1-6}$alkyl; or $C_{1-6}$alkoxy;

provided that
i) when R is a radical of formula (a) and $R_1$ is on position 7, either ring A contains no heteroatom, or it contains one nitrogen atom at position 5, 6 or 8, or two nitrogen atoms at positions 5 and 8;
ii) when R is a radical of formula (b) or (c), then $R_1$ is on position 7;
iii) when R is a radical of formula (d), then $R_1$ is on position 7 and ring A contains either no heteroatom or one nitrogen atom at position 5 or 6;
iv) when $R_1$ is on position 6 or 7; n is 1; $R_2$ is halogen or $C_{1-4}$alkyl; ring A contains no nitrogen atom; ring B is not substituted on position 4; R is a radical of formula (a); and either i) each of $R_3$ and $R_4$, independently, is H or $C_{1-4}$alkyl or ii) $R_3$ and $R_4$ form together with the nitrogen atom to which they are bound a heterocyclic residue, then at least one of $R_a$, $R_b$, $R_c$, $R_d$ and $R_e$ is other than hydrogen or $C_{1-4}$alkyl;
v) when $R_1$ is on position 6 and is —$NH_2$; ring A contains no nitrogen atom; ring B is not substituted on position 4; R is a radical of formula (a); and each of $R_2$, $R_3$, $R_4$, $R_b$. $R_c$, $R_d$ and $R_e$ is hydrogen, then $R_a$ is other than hydrogen or $C_{1-4}$alkyl;

or a physiological hydrolysable derivative thereof, a salt, hydrate and/or solvate thereof.

In another embodiment of the invention, there is provided a compound of formula (II),

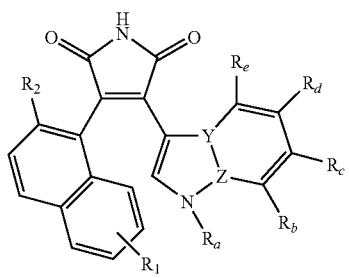

(II)

wherein
either
i) each of Y and Z is —CH═, or
ii) Y is —CH═ and Z is N, or
iii) Y is —N— and Z is —CH═;
and $R_1$, $R_2$, $R_a$, $R_b$, $R_c$, $R_d$ and $R_e$ are as defined hereinabove;
with the proviso that when Z or Y is N, then $R_a$ is hydrogen; or a physiologically hydrolysable derivative thereof, a salt, hydrate and/or solvate thereof.

According to another embodiment there is provided a compound of formula (IIa)

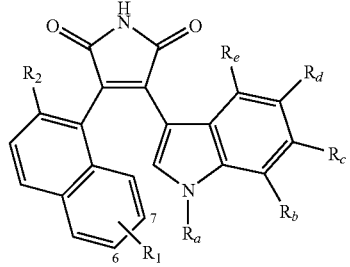

(IIa)

wherein $R_1$, $R_2$, $R_a$, $R_b$, $R_c$, $R_d$ and $R_d$ are as defined hereinabove;
with the proviso that when $R_1$ is on position 6 or 7; $R_2$ is halogen or $C_{1-4}$alkyl; and either i) each of $R_3$ and $R_4$, independently, is H or $C_{1-4}$alkyl or ii) $R_3$ and $R_4$ form together with the nitrogen atom to which they are bound a heterocyclic residue, then at least one of $R_a$, $R_b$, $R_d$, $R_d$ and $R_e$ is other than hydrogen or $C_{1-4}$alkyl;
or a physiologically hydrolysable derivative thereof, a salt, hydrate and/or solvate thereof.

In another embodiment there is provided a compound of formula (IIb) or (IIc)

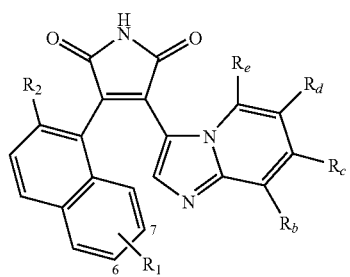

(IIb)

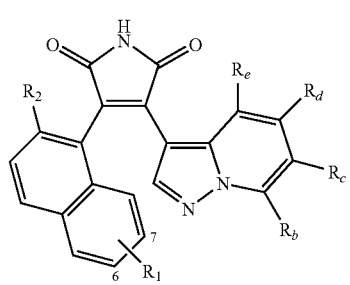

(IIc)

wherein $R_1$, $R_2$, $R_b$, $R_c$, $R_d$ and $R_e$ are as defined hereinabove;
or a physiologically hydrolysable derivative thereof, a salt, hydrate and/or solvate thereof.

In yet another embodiment of the invention, there is provided a compound of formula (III),

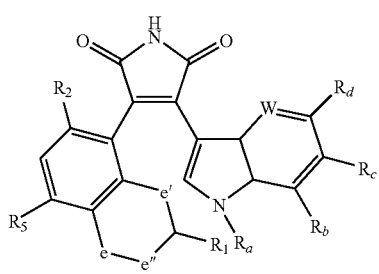

(III)

wherein
each of e, e' and e", independently, is —CH= or N,
either W is a —C—$R_e$, one of e, e' and e" is N and the other two are each —CH=;
or W is —C—$R_e$, each of e and e' is N, and e" is —CH=;
or W is —N=, and each of e, e' and e" is —CH=;
or W is —N=, e is N, and each of e' and e" is —CH=;
or W is —N=, each of e and e' is —CH= and e" is N;
$R_1$, $R_2$ $R_a$, $R_b$, $R_c$, $R_d$ and $R_e$ are as defined hereinabove;
$R_5$ is hydrogen or halogen;
or a physiologically hydrolysable derivative thereof, a salt, hydrate and/or solvate thereof.
Halogen may be F, Cl, Br or I, preferably F, Cl or Br.
Alkyl or alkoxy, as a group or present in a group, may be straight or branched.
When an alkyl or alkoxy is substituted e.g. by OH, $NH_2$ or an heterocyclic residue the substituent is preferably at the terminal position of the alkyl or alkoxy chain.
When alkyl or alkoxy, as a group or a moiety present in a group, is substituted by an halogen, it may be substituted by 1 to 5 halogen, e.g. $CH_2F$, $CHF_2$, $CF_3$, $CHF_2$—$CH_2$—O— or $CF_3$—$CH_2$—O—. The halogen is preferably at the end of the alkyl chain.
When a substituent, e.g. $R_a$ or $R_b$, $R_c$, $R_d$, comprises $C_{1-2}$alkoxy optionally interrupted by one oxygen atom ($R_a$) or by one or two oxygen atom(s) ($R_b$, $R_c$, $R_d$), then the $C_{1-12}$alkoxy is preferably terminated by —O—$CH_3$.
When a substituent, e.g. $R_3$ or $R_4$, is $C_{2-4}$alkenyl, the double bound may be at any position in the alkyl chain, preferably at the terminal position of the chain.
The carbocyclic group, e.g. as formed by $R_b$ and $R_c$ together with the carbon atoms to which they are attached, contains at least one double bound and may contain 5 to 8 carbons, preferably 5 to 7 carbons, more preferably 6 carbons. Optionally it contains two or more double bounds, preferably it is aromatic, e.g. aryl.
The $C_{4-8}$cycloalkyl, e.g. as $R_a$, may contain 4 to 8 carbons, preferably 5 to 7 carbons, more preferably 6 carbons. Optionally it is fused to another five to eight membered saturated, unsaturated or aromatic cyclic or heterocyclic ring.
By heterocyclic residue, e.g. as $R_a$ or formed by $R_3$ and $R_4$ together with N to which they are bound, or by $R_a$ and $R_b$ together with the

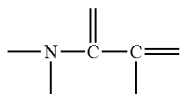

chain to which they are attached to form a ring, respectively, or as a substituent of alkyl or alkoxy, is meant a five to eight, preferably five to six, membered saturated, unsaturated or aromatic heterocyclic ring comprising 1 or 2 heteroatoms, preferably selected from N, O and S. The heterocyclic residue, e.g. as $R_a$ is optionally fused to another five to eight membered saturated, unsaturated or aromatic cyclic or heterocyclic ring, preferably to a 6 membered saturated, unsaturated or aromatic cyclic or heterocyclic ring, more preferably to a 6 membered aromatic cyclic or heterocyclic ring. In case the heterocyclic residue is a non aromatic cycle and is a substituent of an alkyl chain, e.g. as $R_a$, then the alkyl chain comprises at least 2 carbon atoms and the heterocyclic residue is not linked to the first carbon atom of the alkyl chain. In case the heterocyclic residue is a substituent of an alkyl chain, e.g. as $R_a$, it may be linked to the alkyl chain through either a/the ring heteroatom, e.g. N, or through a ring carbon atom.

In case the heterocyclic residue is a non aromatic cycle and is a substituent of an alkoxy chain, e.g. as any of $R_b$, $R_c$ or $R_d$, and is linked to the alkoxy chain through a/the ring heteroatom (e.g. N atom), then the alkoxy chain contains at least 2 carbon atoms and the heterocyclic residue is not linked to the first carbon atom of the alkoxy chain.

According to the invention, the heterocyclic residue is optionally substituted, on one or more ring carbon atoms and/or, e.g. in the case of the heterocyclic residue formed by $R_3$ and $R_4$ and the N atom to which they are attached, on a ring heteroatom when present.

Examples of a substituent on a ring carbon atom include e.g. $C_{1-6}$alkyl, e.g. $CH_3$;

$C_{3-6}$cycloalkyl, e.g. cyclopropyl, optionally further substituted by $C_{1-4}$alkyl;

wherein p is 1, 2 or 3, preferably 1; $CF_3$; halogen; OH; $NH_2$; —$CH_2$—$NH_2$; —$CH_2$—OH; piperidin-1-yl; or pyrrolidinyl.

Examples of a substituent on a ring nitrogen atom are e.g. $C_{1-6}$alkyl; acyl, e.g. $R'_x$—CO wherein $R'_x$ is H, $C_{1-6}$alkyl or phenyl optionally substituted by $C_{1-4}$alkyl, $C_{1-4}$alkoxy or amino, e.g formyl; $C_{3-6}$cycloalkyl; $C_{3-6}$cycloalkyl-$C_{1-4}$alkyl; phenyl; phenyl-$C_{1-4}$alkyl e.g. benzyl; a heterocyclic residue, e.g. as disclosed above, e.g. an aromatic heterocyclic residue comprising 1 or 2 nitrogen atoms; or a residue of formula β

(β)

wherein $R_5$ is $C_{1-4}$alkylene or $C_{2-4}$alkylene interrupted by 0 and Z is OH, $NH_2$, $NH(C_{1-4}$alkyl$)$ or $N(C_{1-4}$alkyl$)_2$.

When the substituent on a cyclic nitrogen is a heterocyclic residue, it may be a five or six membered saturated, unsaturated or aromatic heterocyclic ring comprising 1 or 2 heteroatoms, preferably selected from N, O and S. Examples include e.g. 3- or 4-pyridyl, piperidyl, e.g. piperidin-1-yl, 3- or 4-piperidyl, homopiperidyl, piperazinyl, homopiperazinyl, pyrimidinyl, morpholin-4-yl, imidazolyl, imidazolidinyl, pyrrolyl or pyrrolidinyl.

When $R_a$ is an heterocyclic residue, suitable examples of substituent include e.g. $C_{1-4}$alkyl, preferably on one ring carbon atom.

When an heterocyclic residue is formed by $R_a$ and $R_b$ together with the

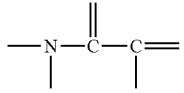

chain to which they are attached, suitable examples of substituent include e.g. $C_{1-4}$alkyl.

Suitable examples of heterocyclic residue include pyridyl, e.g. 3- or 4-pyridyl, piperidyl, e.g. piperidin-1-yl, 3- or 4-piperidyl, homopiperidyl; imidazolyl, e.g. imidazol-1-yl; imidazolidinyl; piperazinyl; homopiperazinyl; morpholin-4-yl; pyridinyl; isoquinolinyl, e.g. 4-isoquinolinyl; pyrrolyl or pyrrolidinyl optionally substituted, e.g. mono- or polysubstituted, e.g. 4-methyl-piperazin-1-yl. The preferred heterocyclic residues are imidazolyl, piperazinyl, isoquinolinyl, optionally substituted.

Preferably $R_3$ and $R_4$ form a piperazinyl, more preferably a substituted piperazinyl, even more preferably a piperazinyl substituted by $C_{1-4}$alkyl, e.g. on the N atom.

Suitable examples for $R_a$ include, isoquinolinyl, e.g. 4-isoquinolinyl.

Suitable examples for substituent of alkyl as $R_a$ include imidazol, e.g. imidazol-1-yl.

Suitable examples for substituent of alkoxy as $R_b$ include imidazol, e.g. imidazol-1-yl, piperazine optionally substituted e.g. by $C_{1-4}$alkyl, e.g. on position 4, e.g. 4-methyl-piperazin-1-yl.

Preferably the heterocyclic residue which is formed by $R_a$ and $R_b$ together with the

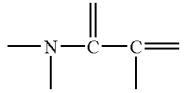

chain to which they are attached, is a piperazinyl or quinolinyl.

The compounds of the invention may exist in free form or in salt form, e.g. addition salts with e.g. organic or inorganic acids, for example, hydrochloric acid, acetic acid, trifluoroacetic acid.

It will be appreciated that the compounds of the invention may exist in the form of optical isomers, racemates or diastereoisomers. For example, a ring carbon atom bearing a substituent in the position 3 of the piperazinyl residue is asymmetric and may have the R- or S-configuration. It is to be understood that the present invention embraces all enantiomers and their mixtures. Enantiomers are preferred over racemates. Similar considerations apply in relation to starting materials exhibiting asymmetric carbon atoms as mentioned.

According to the invention, the following significances are preferred individually or in any sub-combination:

1. R is a radical of formula (a);
2. when R is a radical of formula (a), $R_a$ is H; $C_{1-6}$alkyl, e.g. methyl; $C_{1-6}$alkyl substituted by OH, NH$_2$, NHC$_{1-4}$alkyl, N(di-C$_{1-4}$alkyl)$_2$, heterocyclic group or $C_{1-12}$alkoxy optionally interrupted by one O atom and optionally substituted by OH or NH$_2$; or optionally substituted heterocyclic residue, e.g. pyridinyl or quinolinyl; or $R_a$ and $R_b$ form together with the

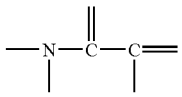

chain to which they are attached a heterocyclic residue, e.g. piperazinyl, optionally substituted by $C_{1-4}$alkyl;
3. when R is a radical of formula (a), each of $R_b$, $R_e$ and $R_d$, independently, is H; halogen; $C_{1-6}$alkyl, e.g. methyl, ethyl; $C_{1-6}$alkyl substituted by $C_{1-12}$alkoxy optionally interrupted by one or two oxygen atom(s); $C_{1-15}$alkoxy optionally interrupted by one or two oxygen atom(s) and optionally substituted by OH, NH$_2$, halogen (e.g. CH$_2$F, CHF$_2$, CF$_3$), or by or optionally substituted heterocyclic group; carbamoyl-$C_{1-6}$alkoxy; mono($C_{1-4}$alkyl)carbamoyl-$C_{1-6}$alkoxy; di($C_{1-4}$alkyl)$_2$-carbamoyl-$C_{1-6}$alkoxy; carboxy-$C_{1-6}$alkoxy; or $C_{1-6}$alkoxy-carbon;
4. when R is a radical of formula (a), each of $R_b$, $R_e$ and $R_d$, independently, is of formula —(CH$_2$)$_o$—NHR$_v$ wherein R$_v$ is hydrogen; $C_{1-4}$alkylC$_{1-6}$alkoxy, e.g. $C_{1-4}$alkyl-OCH$_3$; $C_{1-4}$alkyl-NH—$C_{1-4}$alkyl; or $C_{1-4}$alkyl-N(di-$C_{1-4}$alkyl)$_2$, e.g. $C_{1-4}$alkyl-N(CH$_3$)$_2$; and o is 1 or 2; and $R_e$ is H or $C_{1-4}$alkyl;
5. when R is a radical of formula (a), each of $R_b$, $R_e$ and $R_e$, independently, is of formula O—(CH$_2$)$_p$—NR$_x$R$_y$, wherein each of R$_x$ and R$_y$, independently, is hydrogen or $C_{1-4}$alkyl; and p is 2, 3 or 4;
6. when R is a radical of formula (a), $R_a$ and $R_b$ form together with the

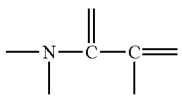

chain to which they are attached a heterocyclic group comprising at least one nitrogen atom and which is optionally substituted e.g. pyridinyl or quinolinyl, and each of $R_c$, $R_d$ and $R_e$, independently, is hydrogen; halogen; $C_{1-6}$alkyl; or $C_{1-6}$alkoxy;
7. when R is a radical of formula (a), $R_c$ and $R_d$, independently, is hydrogen; halogen; $C_{1-6}$alkyl; or $C_{1-15}$alkoxy optionally interrupted by one or two oxygen atom(s) and optionally substituted by OH;
8. when R is a radical of formula (a), $R_e$ is hydrogen;
9. when R is a radical of formula (a), $R_b$ and $R_c$ form together with the carbon atoms to which they are attached a $C_{5-8}$carbocyclic group and $R_d$ and $R_e$ are both hydrogen;
10. when R is a radical of formula (a), $R_1$ is in position 7;
11. when R is a radical of formula (a), $R_2$ is H; halogen, e.g. Cl; or $C_{1-6}$alkyl, e.g. methyl;
12. when R is a radical of formula (a), n is 1;
13. when R is a radical of formula (a), each of $R_3$ and $R_4$ independently, is hydrogen; $C_{1-6}$alkyl, e.g. methyl; $C_{1-6}$alkyl substituted by halogen, or $C_{1-6}$alkoxy; C cycloalkyl; $C_{2-4}$alkenyl; or carboxy-$C_{1-6}$alkoxy; or $R_3$ and $R_4$ form together with the nitrogen atom to which they are bound a heterocyclic residue, e.g. piperazinyl or pyrrolidinyl, optionally substituted by $C_{1-4}$alkyl, e.g. on the N ring atom, e.g. N-methyl piperazinyl;
14. when R is a radical of formula (a), ring A contains one N atom on position 5, 6 or 8, and each of $R_a$, $R_b$, $R_e$ and $R_d$ independently, is hydrogen; or $C_{1-6}$-alkyl;

15. when R is a radical of formula (a), ring A contains one N atom on position 5, 6 or 8, each of $R_3$ and $R_4$ independently, is hydrogen; $C_{1-6}$alkyl, e.g. methyl; $C_{2-6}$alkenyl; or $R_3$ and $R_4$ form together with the nitrogen atom to which they are bound a heterocyclic residue;
16. when R is a radical of formula (a), ring A contains one N atom on position 5, 6 or 8, and $R_2$ is hydrogen or halogen, e.g. Cl;
17. when R is a radical of formula (a), ring A contains one N atom on position 5, 6 or 8, and ring B contains hydrogen or halogen on position 4;
18. when R is a radical of formula (a), ring A contains two N atoms on positions 5 and 8, and $R_2$ is H; halogen, e.g. Cl; or OH;
19. when R is a radical of formula (a), ring A contains two N atoms on positions 5 and 8, and each of $R_3$ and $R_4$, independently, is H; or $C_{1-6}$alkyl, e.g. methyl;
20. R is a radical of formula (b);
21. R is a radical of formula (c);
22. R is a radical of formula (d);
23. when R is a radical of formula (b), (c) or (d), each of $R_a$, $R_b$, $R_c$ and $R_d$, independently, is H; or $C_{1-6}$alkyl, e.g. methyl;
24. when R is a radical of formula (b), (c) or (d), each of $R_3$ and $R_4$, independently, is H; or $C_{1-6}$alkyl; or $R_3$ and $R_4$, from together with the N atom to which they are bound a heterocyclic residue;
25. when R is a radical of formula (b), (c) or (d), $R_2$ is H; or halogen, e.g. Cl;
26. when R is a radical of formula (d), ring A contains one N atom on position 5 and $R_2$ is H; halogen, e.g. Cl.

The present invention also includes a process for the preparation of a compound of formula (I), which process comprises reacting a compound of formula (I')

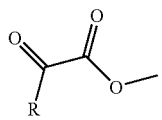

(I')

wherein R is as defined hereinabove, with a compound of formula (I")

R"—CH$_2$—CO—NH$_2$  (I")

wherein R" is

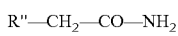

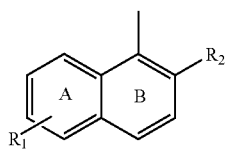

wherein
$R_1$ and $R_2$ are as defined hereinabove,
ring A may contain one or two Nitrogen atoms at positions 5, 6 or 8, and ring B may be substituted by an halogen on position meta vis-à-vis $R_2$;
with the provisos (i), (ii), (iii), (iv) and (v) as indicated above;

and, where required, converting the resulting compound of formula (I) obtained in free form to a salt form or vice versa, as appropriate.

The processes may conveniently be effected in the presence of a strong base, e.g. t-BuOK, e.g. as disclosed in WO02/38561, WO2005/068454 and WO2005/068455, the contents of which being incorporated herein by reference, and as illustrated in the Examples.

Compounds of formula (I') and (I") may be prepared in accordance with known methods, e.g. as disclosed in WO02/38561 or WO 03/08259, the contents of which being incorporated herein by reference, and as illustrated in the Examples.

Compounds of formula (I') and (I") may be prepared in accordance with known methods, e.g. as disclosed in WO02/38561 or WO 03/08259, the contents of which being incorporated herein by reference, and as illustrated in the Examples.

Furthermore there is provided a process for the preparation of a compound of formula (II), which process comprises reacting a compound
of formula (II')

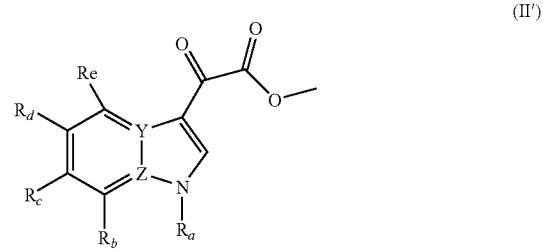

(II')

wherein $R_a$ to $R_e$, Y and Z are as defined hereinabove,
with the proviso that when Z or Y is nitrogen atom, then $R_a$ is hydrogen with a compound of formula (II")

$R_2$"—CH$_2$—CO—NH$_2$  (II")

wherein $R_2$" is

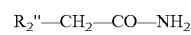

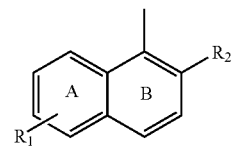

wherein $R_1$ and $R_2$, ring A and ring B are as defined hereinabove, and, where required, converting the resulting compound of formula (II) obtained in free form to a salt form or vice versa, as appropriate.

In another embodiment of the invention there is provided a process for the preparation of a compound of formula (IIa), (IIb) and (IIc) which process comprises reacting a compound of formula (IIa'), (II'b) or (II'c), respectively,

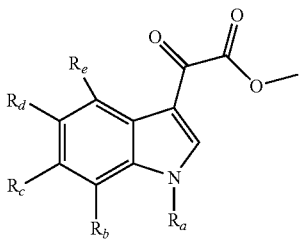
(IIa')

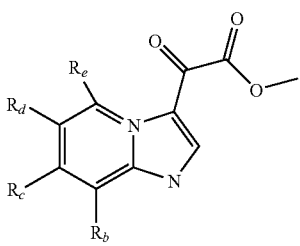
(II'b)

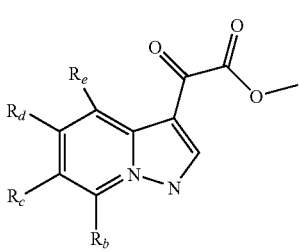
(II'c)

with a compound of formula (II″) as hereinabove defined
and, where required, converting the resulting compound of formula (IIa), (IIb) and (IIc) obtained in free form to a salt form or vice versa, as appropriate.

In yet another embodiment of the invention there is provided a process for the preparation of a compound of formula (III), which process comprises reacting a compound of formula (III')

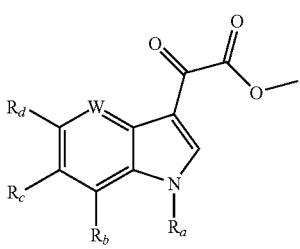
(III')

wherein $R_a$ to $R_d$ and W are as defined hereinabove,
with a compound of formula (III″)

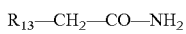
(III″)

wherein $R_{13}$ is

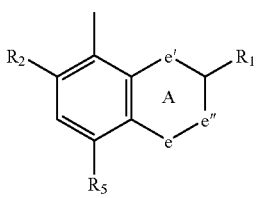

wherein
$R_1$, $R_2$ and $R_5$ are as defined hereinabove,
e, e' and e″ are as defined hereinabove and
ring A is an aromatic ring,
and, where required, converting the resulting compound of formula (III') obtained in free form to a salt form or vice versa, as appropriate.

Insofar as the production of the starting materials is not particularly described, the compounds are known or may be prepared analogously to methods known in the art or as described hereafter.

The following examples are illustrative of the invention without any limitation.

| | |
|---|---|
| RT = | room temperature |
| THF = | tetrahydrofuran |
| DMF = | dimethylformamide |
| EtOAc = | ethylacetate |
| KOtBu = | potassium tertiary butoxide |
| FCC = | flash column chromatography |
| HPLC = | high performance liquid chromatography |
| TLC = | thin layer chromatography |

EXAMPLE 1

3-{2-Chloro-7-[(2-fluoro-ethylamino)-methyl]-naphthalen-1-yl}-4-(1-methyl-1H-indol-3-yl)-pyrrole-2,5-dione

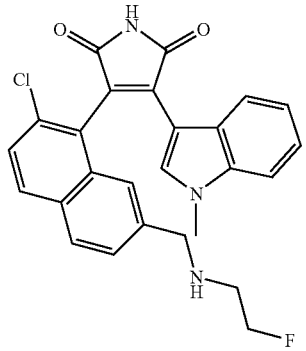

Trifluoroacetic acid (0.5 ml) is added at RT under an atmosphere of argon to a solution of 7-chloro-8-[4-(1-methyl-1H-indol-3-yl)-2,5-dioxo-2,5-dihydro-1H-pyrrol-3-yl]-naphthalen-2-yl-methyl}-(2-fluoro-ethyl)-carbamic acid tert-butyl ester (118 mg, 0.20 mmol) in $CH_2Cl_2$ (5 ml). After 1 h at RT, the reaction mixture was concentrated, and the residue was purified by reversed phase HPLC to yield the title compound as its trifluoroacetate salt. $^1$H NMR ($d_6$-DMSO, 400 MHz): δ 2.45-3.10 (br m, 2H), 3.82 (s, 3H), 4.22-4.28 (br m, 2H), 4.48-4.64 (m, 2H), 6.10 (d, J=9 Hz, 1H), 6.46-6.50 (m, 1H), 6.97-7.02 (m, 1H), 7.38 (d, J=9 Hz, 1H), 7.58-7.62 (m, 1H), 7.72 (d, J=10 Hz, 1H), 7.88 (s, 1H), 8.05-8.18 (m, 3H), 9.0-9.3 (br, 2H). ES$^+$-MS: 462, 464 [M+H+ $H_2O$]$^+$. ES$^-$-MS: 460, 462 [M–H]$^-$.

Preparation of {7-Chloro-8-[4-(1-methyl-1H-indol-3-yl)-2,5-dioxo-2,5-dihydro-1H-pyrrol-3-yl]-naphthalen-2-ylmethyl}-(2-fluoro-ethyl)-carbamic acid tert-butyl ester (8-Carbamoylmethyl-7-chloro-naphthalen-2-ylmethyl)-(2-fluoro-ethyl)-carbamic acid tert-butyl ester (80 mg, 0.20 mmol) and (1-methyl-1H-indol-3-yl)-oxo-acetic acid methyl ester (57 mg, 0.26 mmol) are dissolved under an atmosphere of argon in dry THF (4 ml). Activated molecular sieves 3 Å (100 mg) is added. After 10 minutes at RT, a solution of 1.0 M KOtBu in THF (0.61 ml, 0.61 mmol) is added in one portion. The reaction mixture is diluted with EtOAc and poured into a saturated aqueous NH$_4$Cl solution. The organic layer is separated, washed with brine, dried over Na$_2$SO$_4$ and concentrated. The residue is directly used in the next reaction. ES$^+$-MS: 579.2, 580.5 [M+H+H$_2$O]$^+$. ES$^-$-MS: 560.2, 561.5 [M–H]$^-$.

Preparation of (8-Carbamoylmethyl-7-chloro-naphthalen-2-ylmethyl)-(2-fluoro-ethyl)-carbamic acid tert-butyl ester Carbonyl diimidazole (95 mg, 0.58 mmol) was added at RT under an atmosphere of argon to a solution of (7-{[tert-butoxycarbonyl-(2-fluoro-ethyl)-amino]-methyl}-2-chloro-naphthalen-1-yl)-acetic acid (210 mg, 0.53 mmol) in DMF (2.0 ml). After 2 h at RT, concentrated aqueous ammonia (4.3 ml) is added, and the mixture is stirred for 15 minutes at RT. The emulsion is extracted with EtOAc. The organic layer is washed with brine and dried over Na$_2$SO$_4$. After concentration, the residue is purified by FCC (EtOAc) to yield the title compound. $^1$H NMR (d$_6$-DMSO, 400 MHz): δ 1.38+1.46 (2x br s, 9H), 3.3-3.6 (br m, 2H), 4.08 (s, 2H), 4.40-4.65 (br m, 2H), 4.61 (s, 2H), 7.02 (br s, NH), 7.42 (br d, J=9 Hz, 1H), 7.48-7.58 (br m, 3H), 7.80-7.90 (br m, 2H), 7.95 (br d, J=9 Hz, 1H). ES$^+$-MS: 412.3, 414.2 [M+H+H$_2$O]$^+$. ES$^-$-MS: 393.3, 395.3 [M–H]$^-$.

Preparation of (7-{[tert-Butoxycarbonyl-(2-fluoro-ethyl)-amino]-methyl}-2-chloro-naphthalen-1-yl)-acetic acid A aqueous solution of NaOH (2 M, 0.59 ml, 1.17 mmol) was added at RT under an atmosphere of argon to a solution of (7-{[tert-butoxycarbonyl-(2-fluoro-ethyl)-amino]-methyl}-2-chloro-naphthalen-1-yl)-acetic acid ethyl ester (249 mg, 0.59 mmol) in dioxane (2.7 ml). The slightly turbid mixture is rendered clear by the addition of 6 drops of MeOH. After warming to 45° C. for 2.5 h, HPLC analysis indicated complete consumption of starting material. Removal of solvent yielded a residue, which was taken up in water. After acidification to pH 4 by the addition of 1 M HCl, the mixture was extracted with EtOAc. The organic layer was washed with brine, dried over Na$_2$SO$_4$ and concentrated. The crude product was used directly in the next step. ES$^+$-MS: 413.3, 415.5 [M+H+H$_2$O]$^+$. ES$^-$-MS: 394.2, 396.2 [M–H]$^-$.

Preparation of (7-{[tert-Butoxycarbonyl-(2-fluoro-ethyl)-amino]-methyl}-2-chloro-naphthalen-1-yl)-acetic acid ethyl ester Tert-butyloxycarbonyl anhydride (135 mg, 0.62 mmol) is added at RT to a solution of 7-{[(2-fluoro-ethyl)-amino]-methyl}-2-chloro-naphthalen-1-yl)-acetic acid ethyl ester (200 mg, 0.62 mmol) in CH$_2$Cl$_2$ (6 ml). After stirring at RT for 2 h, TLC analysis indicates complete consumption of starting material. Removal of solvent yielded the crude reaction product, which was purified by FCC (EtOAc/hexanes 3:2) to afford the title compound. $^1$H NMR (CDCl$_3$, 400 MHz): δ 1.29 (t, J=8.4 Hz, 3H), 1.48+1.55 (2x br s, 9H), 3.40-3.62 (br m, 2H), 4.18 (q, J=8.4 Hz, 2H), 4.29 (s, 2H), 4.40-4.70 (br m, 2H), 4.72 (br s, 2H), 7.35-7.48 (br m, 1H), 7.49 (d, J=9 Hz, 1H), 7.72 (d, J=9 Hz, 1H), 7.73 (s, 1H), 7.82 (d, J=9 Hz, 1H). ES$^+$-MS: 441.3, 443.6 [M+H+H$_2$O]$^+$.

Preparation of (7-{[(2-fluoro-ethyl)-amino]-methyl}-2-chloro-naphthalen-1-yl)-acetic acid ethyl ester 2-Fluoroethylamine hydrochloride (94 mg, 0.94 mmol) is added under an atmosphere of argon to a solution of (2-chloro-7-formyl-naphthalen-1-yl)-acetic acid ethyl ester (200 mg, 0.72 mmol) in 7.6 ml of THF. Triethylamine (0.13 ml, 0.94 mmol) is added, and the mixture is stirred at RT for 18 h, before a solution of sodium cyanoborohydride (50 mg, 0.80 mmol) in MeOH (2.0 ml) and glacial acetic acid (0.21 ml, 3.61 mmol) are added. After stirring at RT for 1 h, TLC analysis indicates complete consumption of starting material. The reaction mixture is diluted with water and adjusted to pH 8 by the addition of a 1 M aqueous solution of NaHCO$_3$. Extraction with EtOAc, washing with brine, drying over Na$_2$SO$_4$ and removal of solvent yields the crude reaction product. Purification by FCC (EtOAc/MeOH 9:1) affords the title compound. $^1$H NMR (CDCl$_3$, 400 MHz): δ 1.26 (t, J=8.4 Hz, 3H), 2.92-3.04 (m, 2H), 4.06 (s, 2H), 4.19 (q, J=8.4 Hz, 2H), 4.32 (s, 2H), 4.52-4.68 (m, 2H), 7.48 (d, J=9 Hz, 1H), 7.51-7.53 (m, 1H), 7.73 (d, J=9.4 Hz, 1H), 7.82 (d, J=9 Hz, 1H), 7.88 (s, 1H). ES$^+$-MS: 324.2, 326.1 [M+H]$^+$.

Preparation of (2-Chloro-7-formyl-naphthalen-1-yl)-acetic acid ethyl ester (2-Chloro-7-cyano-naphthalen-1-yl)-acetic acid ethyl ester (5.53 g, 20.20 mmol) is dissolved in a mixture of water (70 ml), pyridine (130 ml) and glacial acetic acid (70 ml). Sodium hypophosphite (17.13 g, 161.62 mmol) and Raney nickel (13 g) are added at RT. The reaction mixture is heated to 100° C. for 1 h. TLC analysis indicates complete consumption of starting material. The reaction mixture is cooled to RT, filtered through Celite and concentrated on a rotary evaporator. The residue is taken up in 2 M aqueous HCl. Extraction with EtOAc, removal of solvent and purification by FCC (hexane/EtOAc 5:1) yields the title compound. $^1$H NMR (CDCl$_3$, 400 MHz): δ 1.28 (t, J=8.8 Hz, 3H), 4.22 (q, J=8.8 Hz, 2H), 4.39 (s, 2H), 7.68 (d, J=9.9 Hz, 1H), 7.83 (d, J=9.9 Hz, 1H), 7.95-8.03 (m, 2H), 8.48 (s, 1H), 10.2 (s, 1H). ES$^-$-MS: 275.3, 277.3 [M+H]$^+$.

Preparation of (2-Chloro-7-cyano-naphthalen-1-yl)-acetic acid ethyl ester (2-Chloro-7-trifluoromethanesulfonyloxy-naphthalen-1-yl)-acetic acid ethyl ester (9.30 g, 23.43 mmol) is dissolved in DMF (80 ml) under an atmosphere of argon. Palladium(0) tetrakis(triphenylphosphane) (1.08 g, 0.9375 mmol) and zinc (II) cyanide (5.50 g, 46.87 mmol) are added. The reaction mixture is heated to 125° C. After 1 h, TLC analysis indicates complete consumption of starting material. The suspension is cooled to RT and poured onto water. After stirring for 15 minutes, filtration and concentration affords the crude reaction product. Purification by FCC (hexane/EtOAc 4:1) affords the title compound. $^1$H NMR (CDCl$_3$, 400 MHz): δ 1.26 (t, J=8.8 Hz, 3H), 4.19 (q, J=8.8 Hz, 2H), 4.28 (s, 2H), 7.62-7.66 (m, 2H), 7.79 (d, J=9.9 Hz, 1H), 7.92 (d, J=9.9 Hz, 1H), 8.32 (s, 1H). ES$^+$-MS: 274.2 [M+H]$^+$.

Preparation of (2-Chloro-7-trifluoromethanesulfonyloxy-naphthalen-1-yl)-acetic acid ethyl ester (2-Chloro-7-hydroxy-naphthalen-1-yl)-acetic acid ethyl ester (8.03 g, 30.33 mmol) is dissolved under an atmosphere of argon in pyridine (60 ml). After cooling to 0° C., trifluoromethanesulfonic acid anhydride (5.50 ml, 33.36 mmol) is added dropwise during 15 minutes. After stirring at 0° C. for 15 minutes and at RT for 1 h, TLC analysis indicates complete consumption of starting material. The reaction mixture is poured into 1 M aqueous $NaHCO_3$ solution. After extraction with EtOAc, washing with brine and drying of the organic layer over $Na_2SO_4$, concentration yields the crude reaction product. Purification by FCC (hexane/EtOAc 4:1) affords the title compound. $^1$H NMR ($CDCl_3$, 400 MHz): δ 1.13 (t, J=9.4 Hz, 3H), 4.08 (q, J=9.4 Hz, 2H), 4.15 (s, 2H), 7.28-7.30 (m, 1H), 7.48 (d, J=11 Hz, 1H), 7.69 (d, J=11 Hz, 1H), 7.72 (m, 1H), 7.82 (d, J=11 Hz, 1H). $ES^+$-MS: 414.2, 416.0, 397.1 $[M+H]^+$.

Preparation of (2-Chloro-7-hydroxy-naphthalen-1-yl)-acetic acid ethyl ester (2-Chloro-7-methoxy-naphthalen-1-yl)-acetic acid ethyl ester (12.0 g, 43.10 mmol) and tetrabutylammonium iodide (20.7 g, 56.04 mmol) are dissolved under an atmosphere of argon in $CH_2Cl_2$ (240 ml). The reaction mixture is cooled to −78° C. and a 1 M solution of $BBr_3$ in $CH_2Cl_2$ (108 ml, 107.77 mmol) is added during 30 minutes. After stirring at −78° C. for 15 minutes and at RT for 1 h, TLC analysis indicates complete consumption of starting material. A sat. aqueous solution of $NaHCO_3$ (8 ml) is carefully added. The organic layer is separated, washed with brine, dried over $Na_2SO_4$ and concentrated. Purification by FCC (hexane/EtOAc 4:1 to 3:2) yields the title compound. $^1$H NMR ($CDCl_3$, 400 MHz): δ 1.51 (t, J=9.9 Hz, 3H), 4.43 (q, J=9.9 Hz, 2H), 4.48 (s, 2H), 6.28-6.36 (br, 1H), 7.29-7.32 (m, 1H), 7.48-7.49 (m, 1H), 7.58 (d, J=10 Hz, 1H), 7.89 (d, J=10 Hz, 1H), 7.96 (d, J=10 Hz, 1H). $ES^+$-MS: 265.2, 267.2 $[M+H]^+$.

Preparation of (2-Chloro-7-methoxy-naphthalen-1-yl)-acetic acid ethyl ester

A mixture of [2-Chloro-7-methoxy-3,4-dihydro-2H-naphthalen-(1 E/Z)-ylidene]-acetic acid ethyl ester and of (2-Chloro-7-methoxy-3,4-dihydro-naphthalen-1-yl)-acetic acid ethyl ester (26.82 g, 95.52 mmol) is dissolved under an atmosphere of argon in dioxane (280 ml). 2,3-Dichloro-5,6-dicyano-p-benzoquinone (DDQ, 47.70 g, 210.16 mmol) is added, and the reaction mixture is refluxed for 2 h. TLC analysis indicates complete conversion of starting material. After cooling to RT, addition of MeOH renders the reaction mixture homogeneous. Silica gel (250 g) is added, and the solvent is removed by rotary evaporation. Purification by FCC (hexane/EtOAc 9:1) yields the title compound. $^1$H NMR ($CDCl_3$, 400 MHz): δ 1.24 (t, J=8.8 Hz, 3H), 3.95 (s, 3H), 4.19 (q, J=8.8 Hz, 2H), 4.28 (s, 2H), 7.16-7.19 (m, 1H), 7.22 (s, 1H), 7.38 (d, J=10 Hz, 1H), 7.68 (d, J=10 Hz, 1H), 7.75 (d, J=10 Hz, 1H). $ES^+$-MS: 279.2, 281.2 $[M+H]^+$.

Preparation of (2-Chloro-7-methoxy-3,4-dihydro-naphthalen-1-yl)-acetic acid ethyl ester (2-Chloro-1-hydroxy-7-methoxy-1,2,3,4-tetrahydro-naphthalen-1-yl)-acetic acid ethyl ester (42.7 g, 142.9 mmol) is dissolved under an atmosphere of argon in pyridine (250 ml). Trifluoromethanesulfonic acid anhydride (30.7 ml, 185.8 mmol) is added during 30 minutes, while keeping the temperature at 25° C. with occasional cooling with a ice bath. After addition is complete, the reaction mixture is warmed to 50° C. for 2 h. TLC analysis indicates complete conversion of starting material. 2 M aqueous HCl (100 ml) is carefully added, and then the reaction mixture is concentrated to dryness on the rotary evaporator. The residue is taken up in 2 M aqueous HCl (100 ml) and extracted with EtOAc. The organic layer is dried over $Na_2SO_4$ and concentrated. Purification by FCC (EtOAc) affords the title compound. $ES^+$-MS: 281.2, 283.2 $[M+H]^+$.

Preparation of (2-Chloro-1-hydroxy-7-methoxy-1,2,3,4-tetrahydro-naphthalen-1-yl)-acetic acid ethyl ester A solution of EtOAc (16.1 ml, 164.48 mmol) in THF (250 ml) is slowly added under an atmosphere of argon at −78° C. to a solution of lithium diisopropylamine (prepared from 23.3 ml of diisopropylamine (164.48 mmol) and 102.8 ml of 1.6 M n-BuLi in hexane (164.48 mmol) in THF (250 ml). After stirring at −78° C. for 30 minutes, a solution of 2-chloro-7-methoxy-3,4-dihydro-2H-naphthalen-1-one (31.5 g, 149.53 mmol) in THF (250 ml) is slowly added during 30 minutes. The reaction mixture is stirred at −78° C. for 1 h. TLC analysis indicates complete conversion of starting material. A sat. aqueous solution of $NH_4Cl$ (250 ml) is carefully added to the reaction mixture at −78° C. The mixture is warmed to RT. The organic layer is separated, diluted with EtOAc and washed with brine. After drying over $Na_2SO_4$, the solvent is removed. Purification by FCC (hexane/EtOAc 4:1) yields the title compound. $^1$H NMR ($CDCl_3$, 400 MHz): δ 1.27 (t, J=9.4 Hz, 3H), 2.32-2.48 (m, 2H), 2.78-2.88 (m, 1H), 2.86-3.02 (m, 2H), 3.05-3.14 (m, 1H), 3.82 (s, 3H), 4.18 (q, J=9.4 Hz, 2H), 5.02-5.08 (m, 1H), 6.81-6.84 (m, 1H), 7.03 (d, J=10.5 Hz, 1H), 7.18-7.19 (m, 1H). $ES^+$-MS: 281.3, 283.3 $[M+H-H_2O]^+$.

Preparation of 2-Chloro-7-methoxy-3,4-dihydro-2H-naphthalen-1-one

A solution of 7-Methoxy-3,4-dihydro-2H-naphthalen-1-one (25.6 g, 145.28 mmol) in THF (300 ml) is slowly added under an atmosphere of argon at −78° C. to a solution of lithium diisopropyl amine in THF (300 ml; prepared from 22.6 ml of diisopropylamine (160 mmol) and 100 ml of 1.6 M n-BuLi in hexane (160 mmol)). After 30 minutes at −78° C., a solution of para-tolylsulfonyl chloride (30.5 g, 159.8 mmol) in THF (300 ml) is added during 20 minutes. The dry ice cooling bath is removed, and the reaction mixture is allowed to reach RT. After 1 h, TLC analysis indicates complete consumption of starting material. A sat. aqueous solution of $NH_4Cl$ (100 ml) is added, and the mixture is stirred at RT for 15 minutes. The organic layer is separated, washed with brine, dried over $Na_2SO_4$ and concentrated. Purification by FCC (hexane/EtOAc 3:1) yields the title compound. $^1$H NMR ($CDCl_3$, 400 MHz): δ 2.32-2.52 (m, 2H), 2.82-2.90 (m, 2H), 3.10-3.18 (m, 2H), 3.78 (s, 1H), 4.52-4.58 (m, 1H), 7.01-7.05 (m, 1H), 7.11 (d, J=8.8 Hz, 1H), 7.47-7.48 (m, 1H). $ES^+$-MS: 211.3, 213.3 $[M+H]^+$.

By following the procedures of Example 1, but by using the appropriate starting materials and by omitting the amine protection/deprotection steps in the cases where both $R_3$ and $R_4$ ≠H, the compounds of formula A wherein $R_a$, $R_b$, $R_c$, $R_d$, $R_3$ and $R_4$ are as indicated in Table 1 below, and $R_e$ is H, may be obtained.

TABLE 1

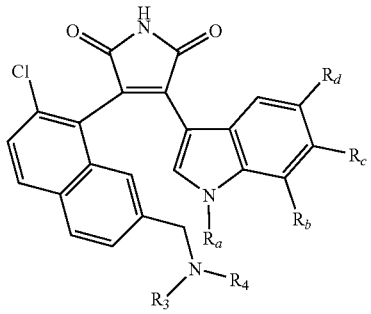

A

| | $R_3$ | $R_4$ | $R_a$ | $R_b$ | $R_c$ | $R_d$ | MS |
|---|---|---|---|---|---|---|---|
| 2. | CH$_3$ | CH$_2$CH$_2$F | CH$_3$ | H | H | H | MH$^+$ 477 |
| 3. | H | CH$_2$CH$_2$F | H | CH$_3$ | H | H | MH$^+$ 463 |
| 4. | H | CH$_2$CH$_2$F | H | H | CH$_3$ | H | MH$^+$ 463 |
| 5. | H | CH$_2$CH$_2$F | H | H | H | CH$_3$ | MH$^+$ 463 |
| 6. | H | CH$_2$CH$_2$F | H | H | H | H | MH$^+$ 449 |
| 7. | CH$_3$ | CH$_2$CH(CH$_2$CH$_2$) | CH$_3$ | H | H | H | MH$^+$ 485 |
| 8. | H | CH$_2$CH(CH$_2$CH$_2$) | CH$_3$ | H | H | H | MH$^+$ 471 |
| 9. | CH$_3$ | CH$_2$CH$_2$OCH$_3$ | CH$_3$ | H | H | H | MH$^+$ 489 |
| 10. | H | CH$_2$CH$_2$OCH$_3$ | CH$_3$ | H | H | H | MH$^+$ 475 |
| 11. | H | CH$_2$CH$_2$OCH$_3$ | H | CH$_3$ | H | H | MH$^+$ 475 |
| 12. | H | CH$_2$CH$_2$OCH$_3$ | H | H | CH$_3$ | H | MH$^+$ 475 |
| 13. | H | CH$_2$CH$_2$OCH$_3$ | H | H | H | CH$_3$ | MH$^+$ 475 |
| 14. | H | CH$_2$CH$_2$OCH$_3$ | H | H | H | H | MH$^+$ 461 |
| 15. | CH$_3$ | CH$_2$CH=CH$_2$ | CH$_3$ | H | H | H | MH$^+$ 471 |
| 16. | H | CH$_2$CH=CH$_2$ | CH$_3$ | H | H | H | MH$^+$ 457 |
| 17. | CH$_3$ | CH(CH$_2$CH$_2$) | CH$_3$ | H | H | H | MH$^+$ 471 |
| 18. | H | CH(CH$_2$CH$_2$) | CH$_3$ | H | H | H | MH$^+$ 457 |
| 19. | CH$_3$ | CH$_3$ | H | OCH$_2$C(O)N(CH$_2$CH$_3$)$_2$ | H | H | MH$^+$ 560 |
| 20. | CH$_3$ | CH$_3$ | | (N)—CH$_2$CH$_2$CH$_2$O—(C) | H | H | MH$^+$ 487 |
| 21. | CH$_2$CH$_2$N(CH$_3$)CH$_2$CH$_2$ | | H | CH$_3$ | H | H | MH$^+$ 500 |
| 22. | CH$_2$CH$_2$N(CH$_3$)CH$_2$CH$_2$ | | H | H | H | H | MH$^+$ 486 |
| 23. | CH$_3$ | CH$_3$ | H | OCH$_2$CH$_2$OCH$_3$ | H | H | MH$^+$ 519 |
| 24. | CH$_3$ | CH$_3$ | H | OCH$_3$ | OCH$_3$ | H | MH$^+$ 491 |
| 25. | CH$_3$ | CH$_3$ | H | OCH$_3$ | CH$_3$ | H | MH$^+$ 475 |
| 26. | CH$_3$ | CH$_3$ | H | CH$_3$ | OCH$_3$ | H | MH$^+$ 475 |
| 27. | CH$_3$ | CH$_3$ | H | | CH$_2$CH$_2$CH$_2$CH$_2$ | H | MH$^+$ 485 |
| 28. | CH$_3$ | CH$_3$ | H | | CHCHCHCH | H | MH$^+$ 481 |
| 29. | CH$_3$ | CH$_3$ | H | OCH$_2$CH$_2$OCH$_3$ | H | H | MH$^+$ 505 |
| 30. | CH$_3$ | CH$_3$ | H | OCH$_2$CH$_2$N(CH$_3$)$_2$ | H | H | MH$^+$ 518 |
| 31. | CH$_3$ | CH$_3$ | H | OCH$_2$CH$_2$OCH$_2$CH$_2$OCH$_3$ | H | H | MH$^+$ 549 |
| 32. | CH$_3$ | CH$_3$ | H | CH$_2$N(H)CH$_2$CH$_2$OCH$_3$ | H | H | MH$^+$ |

TABLE 1-continued

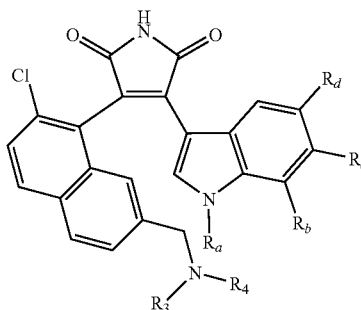

| | $R_3$ | $R_4$ | $R_a$ | $R_b$ | $R_c$ | $R_d$ | MS |
|---|---|---|---|---|---|---|---|
| 33. | $CH_3$ | $CH_3$ | H | $CH_2N(H)CH_2CH_2N(CH_3)_2$ | H | H | MH$^+$ 518 |
| 34. | $CH_3$ | $CH_3$ | H | $OCH_2CH_2OCH_2CF_3$ | H | H | MH$^+$ 531 |
| 35. | $CH_3$ | $CH_3$ | H | $OCH_2CH_2C(CH_3)_2OCH_3$ | H | H | MH$^+$ 572 |
| 36. | $CH_3$ | $CH_3$ | H | $OCH_2CH_3$ | H | H | MH$^+$ 546 |
| 37. | $CH_3$ | $CH_3$ | H | $OCH_3$ | H | H | MH$^+$ 474 |
| 38. | $CH_3$ | $CH_3$ | H | H | $OCH_2CH_2OCH_3$ | H | MH$^+$ 460 |
| 39. | $CH_3$ | $CH_3$ | H | H | $OCH_3$ | H | MH$^+$ 504 |
| 40. | $CH_3$ | $CH_3$ | $CH_2CH_2OCH_3$ | H | H | H | MH$^+$ 460 |
| 41. | $CH_3$ | $CH_3$ | $CH_3$ | $OCH_2CH_2OCH_2CH_2OCH_3$ | H | H | MH$^+$ 488 |
| 42. | $CH_3$ | $CH_3$ | $CH_2CH_2N(CH_3)_2$ | H | H | H | MH$^+$ 562 |
| 43. | $CH_3$ | $CH_3$ | $CH_2CH_2OCH_3$ | $OCH_3$ | H | H | MH$^+$ 501 |
| 44. | $CH_3$ | $CH_3$ | H | $OCH_2C(CH_3)_2OH$ | H | H | MH$^+$ 518 |
| 45. | $CH_3$ | $CH_3$ | $CH_2C(CH_3)_2OH$ | H | H | H | MH$^+$ 518 |
| 46. | $CH_3$ | $CH_3$ | $CH_2CH_2NH_2$ | H | H | H | MH$^+$ 502 |
| 47. | $CH_3$ | $CH_3$ | H | $OCH_2CH_2NH_2$ | H | H | MH$^+$ 473 |
| 48. | $CH_3$ | $CH_3$ | $CH_3$ | $OCH_2C(CH_3)_2OCH_3$ | H | H | MH$^+$ 489 |
| 49. | $CH_3$ | $CH_3$ | H | $OCH_2CH_2F$ | H | H | MH$^+$ 518 |
| 50. | $CH_3$ | $CH_3$ | H | $OCH_2CF_3$ | H | H | MH$^+$ 492 |
| 51. | $CH_3$ | $CH_3$ | H | $OCF_3$ | H | H | MH$^+$ 528 |
| 52. | $CH_3$ | $CH_3$ | H | $OCHF_2$ | H | H | MH$^+$ 514 |
| 53. | H | $CH_3$ | H | H | $OCH_2CH_2OCH_2CH_2OCH_3$ | H | MH$^+$ 510 |
| 54. | H | $CH_3$ | H | $OCH_2CH_2OCH_3$ | H | H | MH$^+$ 534 |
| 55. | H | $CH_3$ | H | H | $OCH_2CH_2OCH_3$ | H | MH$^+$ 490 |
| 56. | H | $CH_3$ | H | $OCH_3$ | H | H | MH$^+$ 490 |
| 57. | H | $CH_3$ | H | $OCH_2CH_2OCH_2CH_2OCH_3$ | H | H | MH$^+$ 446 |
| 58. | $CH_3$ | $CH_3$ | $CH_2CH_2OCH_2CH_2NH_2$ | H | H | H | MH$^+$ 534 |
| 59. | $CH_3$ | $CH_3$ | H | $OCH_2CH_2OCH_2CH_2OH$ | H | H | MH$^+$ 517 |
| 60. | H | $CH_3$ | H | H | $OCH_3$ | H | MH$^+$ 534 |
| 61. | $CH_3$ | $CH_3$ | H | $OCH_2CH_2CH_2NH_2$ | H | H | MH$^+$ 446 |
| 62. | $CH_3$ | $CH_3$ | H | $OCH_2CH_2OCH_2C(CH_3)_3OH$ | H | H | MH$^+$ 503 |
| | | | | | | | MH$^+$ 562 |

TABLE 1-continued

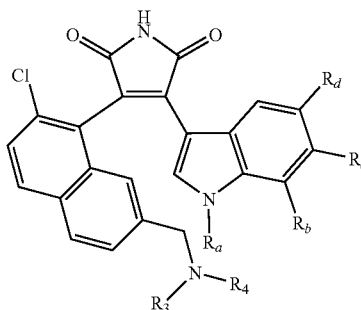

A

| | $R_3$ | $R_4$ | $R_a$ | $R_b$ | $R_c$ | $R_d$ | MS |
|---|---|---|---|---|---|---|---|
| 63. | $CH_3$ | $CH_3$ | H | H | $OCH_2CH_2OCH_2CH_2OCH_3$ | H | $MH^+$ 548 |
| 64. | $CH_3$ | $CH_3$ | $CH_2CH_2OH$ | H | H | H | $MH^+$ 474 |
| 65. | $CH_3$ | $CH_3$ | $CH_2CH_2OCH_2CH_2OCH_3$ | $OCH_3$ | H | H | $MH^+$ 562 |
| 66. | $CH_3$ | $CH_3$ | $CH_2CH_2OCH_2CH_2OH$ | H | H | H | $MH^+$ 518 |
| 67. | $CH_3$ | $CH_3$ | 3-quinolinyl | H | H | H | $MH^+$ 557 |
| 68. | $CH_3$ | $CH_3$ | H | $CH_2OCH_2CH_2OCH_2CH_2OCH_3$ | H | H | $MH^+$ 562 |
| 69. | $CH_3$ | $CH_3$ | H | $CH_2OCH_2CH_2OCH_3$ | H | H | $MH^+$ 518 |
| 70. | $CH_3$ | $CH_3$ | $CH_3$ | $OCH_2C(CH_3)_2OH$ | H | H | $MH^+$ 532 |
| 71. | $CH_3$ | $CH_3$ | $CH_2CH_2OCH_2CH_2OCH_3$ | $CH_3$ | H | H | $MH^+$ 546 |
| 72. | $CH_3$ | $CH_3$ | $CH_2CH_2OCH_2CH_2OCH_3$ | H | H | H | $MH^+$ 532 |
| 73. | $CH_3$ | $CH_3$ | $CH_2CH_2OCH_3$ | $CH_3$ | H | H | $MH^+$ 502 |
| 74. | $CH_3$ | $CH_3$ | H | $OCH_2CH_2OCH_2CH_2OCH_3$ | $CH_3$ | H | $MH^+$ 562 |
| 75. | $CH_3$ | $CH_3$ | H | $OCH_2CH_2OCH_3$ | $CH_3$ | H | $MH^+$ 518 |
| 76. | $CH_3$ | $CH_3$ | H | $OCH_2CH_2OCH_2CH_2OCH_3$ | H | $CH_3$ | $MH^+$ 562 |
| 77. | $CH_3$ | $CH_3$ | H | $OCH_2CH_2OCH_3$ | H | $CH_3$ | $MH^+$ 518 |
| 78. | $CH_3$ | $CH_3$ | H | H | Cl | H | $MH^+$ 464 |
| 79. | $CH_3$ | $CH_3$ | H | H | H | Cl | $MH^+$ 464 |
| 80. | $CH_3$ | $CH_3$ | H | $C(O)OCH_3$ | H | H | $MH^+$ 488 |
| 81. | $CH_3$ | $CH_3$ | $CH_3$ | $OCH_2CH_2OH$ | H | H | $MH^+$ 504 |
| 82. | $CH_3$ | $CH_3$ | H | $OCH_2CH_2CH_2OH$ | H | H | $MH^+$ 504 |
| 83. | $CH_3$ | $CH_3$ | H | H | $OCH_2CH_2OH$ | H | $MH^+$ 490 |
| 84. | $CH_3$ | $CH_3$ | H | H | $OCH_2C(CH_3)_2OH$ | H | $MH^+$ 518 |
| 85. | $CH_3$ | $CH_3$ | H | | H | H | $MH^+$ 572 |
| 86. | $CH_3$ | $CH_3$ | H | $O(CH_2)_4CH_3$ | H | H | $MH^+$ 516 |
| 87. | $CH_3$ | $CH_3$ | H | Cl | H | H | $MH^+$ 464 |
| 88. | $CH_3$ | $CH_3$ | H | $CH_3$ | $OCH_2CH_2OCH_3$ | H | $MH^+$ 518 |
| 89. | $CH_3$ | $CH_3$ | H | $CH_3$ | $OCH_2CH_2OCH_2CH_2OCH_3$ | H | $MH^+$ 562 |
| 90. | $CH_3$ | $CH_3$ | H | $OCH_3$ | H | $OCH_3$ | $MH^+$ 490 |
| 91. | $CH_3$ | $CH_3$ | H | H | $OCH_3$ | $OCH_3$ | $MH^+$ 490 |
| 92. | $CH_3$ | $CH_3$ | H | $OCH_2CH_2$(4-methyl-piperazin-1-yl) | H | H | $MH^+$ 556 |
| 93. | $CH_3$ | $CH_3$ | $CH_3$ | $OCH_2CH_2OCH_2CH_2OH$ | H | H | $MH^+$ |

TABLE 1-continued

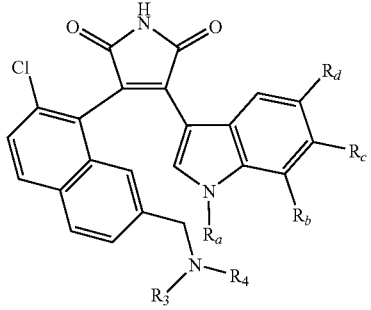

| | $R_3$ | $R_4$ | $R_a$ | $R_b$ | $R_c$ | $R_d$ | MS |
|---|---|---|---|---|---|---|---|
| 94. | CH₃ | CH₃ | H | OCH₂CH₂NH(CH₃) | H | H | MH⁺ 548 |
| 95. | CH₃ | CH₃ | H | O CH₂CH₂(2-imidazol-1-yl) | H | H | MH⁺ 503 |
| 96. | CH₃ | CH₃ | CH₂CH₂(2-imidazol-1-yl) | H | H | H | MH⁺ 540 |
| 97. | CH₃ | CH₃ | H | OCH₂CH₂OCH₃ | H | OCH₃ | MH⁺ 524 |
| 98. | CH₃ | CH₃ | H | OCH₂CH₂OCH₂CH₂OCH₃ | H | CH₃ | MH⁺ 534 |
| 99. | CH₃ | CH₃ | CH₃ | H | OCH₂C(CH₃)₂OH | H | MH⁺ 578 |
| 100. | CH₃ | CH₃ | H | H | OCH₂CH₂OCH₂CH₂OH | H | MH⁺ 532 |
| 101. | CH₃ | CH₃ | H | CH₃ | OCH₂CH₂OCH₃ | CH₃ | MH⁺ 534 |
| 102. | CH₃ | CH₃ | H | CH₃ | OCH₂CH₂OCH₂CH₂OCH₃ | CH₃ | MH⁺ 532 |
| 103. | CH₃ | CH₃ | H | OCH₃ | OCH₂CH₂OCH₂CH₂OCH₃ | H | MH⁺ 576 |
| 104. | CH₃ | CH₃ | H | OCH₃ | OCH₂CH₂OCH₃ | H | MH⁺ 578 |
| 105. | CH₃ | CH₃ | H | CH₃ | OCH₂CH₂OCH₃ | H | MH⁺ 534 |
| 106. | CH₃ | CH₃ | H | CH₃ | OCH₂CH₂OCH₂CH₂OCH₃ | H | MH⁺ 518 |
| 107. | CH₃ | CH₃ | H | OCH₃ | H | F | MH⁺ 562 |
| 108. | CH₃ | CH₃ | H | OCH₂CH₂OCH₃ | H | F | MH⁺ 478 |
| 109. | CH₃ | CH₃ | H | OCH₂CH₂OCH₂CH₂OCH₃ | H | F | MH⁺ 522 |
| 110. | CH₃ | CH₃ | H | H | OCH₂CH₂OCH₂C(CH₃)₂OCH₃ | H | MH⁺ 566 |
| 111. | CH₃ | CH₃ | CH₃ | H | OCH₂CH₂OCH₂C(CH₃)₂OCH₃ | H | MH⁺ 576 |
| 112. | CH₃ | CH₃ | CH₃ | H | OCH₂CH₂OCH₂C(CH₃)₂OH | H | MH⁺ 590 |
| 113. | CH₃ | CH₃ | CH₂CH₂OCH₂CH₂OCH₃ | OCH₂CH₂OCH₂CH₂OCH₃ | H | Cl | MH⁺ 576 |
| 114. | CH₃ | CH₃ | H | OCH₃ | H | Cl | MH⁺ 684 |
| 115. | CH₃ | CH₃ | CH₂CH₂OCH₃ | OCH₂CH₂OCH₃ | H | Cl | MH⁺ 494 |
| 116. | CH₃ | CH₃ | H | OCH₂CH₂OCH₂CH₂OCH₃ | H | Cl | MH⁺ 596 |
| 117. | CH₃ | CH₃ | H | OCH₂CH₂OCH₃ | H | Cl | MH⁺ 582 |
| 118. | CH₃ | CH₃ | CH₃ | H | OCH₂C(CH₃)₂OCH₃ | H | MH⁺ 538 |
| 119. | CH₃ | CH₃ | CH₂CH₂OH | CH₃ | H | H | MH⁺ 546 |
| 120. | CH₃ | CH₃ | CH₂CH₂CH₂OH | H | H | H | MH⁺ 488 |
| 121. | CH₃ | CH₃ | CH₂CH₂CH₂OH | CH₃ | H | H | MH⁺ 488 |
| 122. | CH₃ | CH₃ | CH₂CH₂OH | OCH₃ | H | H | MH⁺ 502 |
| 123. | CH₃ | CH₃ | H | OCH₂CH₂OCH₂CH₂OCH₃ | H | CH₂CH₃ | MH⁺ 504 / 576 |

TABLE 1-continued

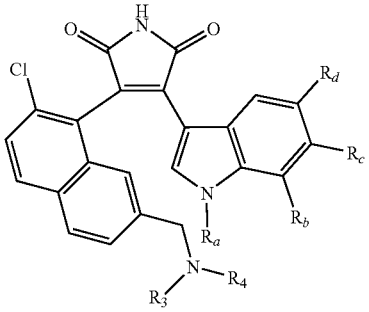

| | $R_3$ | $R_4$ | $R_a$ | $R_b$ | $R_c$ | $R_d$ | MS |
|---|---|---|---|---|---|---|---|
| 124. | $CH_3$ | $CH_3$ | H | $OCH_2CH_2OCH_3$ | H | $CH_2CH_3$ | $MH^+$ 532 |
| 125. | $CH_3$ | $CH_3$ | H | $OCH_3$ | H | $CH_2CH_3$ | $MH^+$ 488 |
| 126. | $CH_3$ | $CH_3$ | $CH_2CH_2OH$ | H | H | $CH_3$ | $MH^+$ 488 |
| 127. | $CH_3$ | $CH_3$ | $CH_2CH_2OH$ | H | $CH_3$ | H | $MH^+$ 488 |
| 128. | $C(O)CH_3$ | $CH_3$ | $CH_3$ | H | H | H | $MH^+$ 472 |
| 129. | $C(O)CH_3$ | $CH_3$ | H | H | H | H | $MH^+$ 458 |

EXAMPLE 130

3-(2-chloro-7-dimethylaminomethyl-naphtalen-1-yl)-4-imidazol[1,2-a]pyridin-3-yl-pyrrole-2,5-dione Preparation of {2-(2-Chloro-7-dimethylaminomethyl-naphthalen-1-yl)-acetamide}: disclosed in WO2005/068454 (example 1)

Addition to Imidazo[1,2-a]pyridin-3-yl-oxo-acetic acid methyl ester as disclosed in Example 1.

By following the procedures of Example 1, but by using the appropriate starting materials, the compounds of formula B wherein $R_{b'}$ and $R_{c'}$ are as indicated in Table 2 below may be obtained.

TABLE 2

B

| | $R_{b'}$ | $R_{c'}$ | MS |
|---|---|---|---|
| 130 | H | H | $MH^+$ 432 |
| 131 | $CH_3$ | H | $MH^+$ 446 |
| 132 | H | $CH_3$ | $MH^+$ 446 |

By following the procedures of Example 130, but by using the appropriate starting materials, the compounds of formula C wherein $R_{b'}$ is as indicated in Table 3 below may be obtained.

TABLE 3

C

| | $R_{b'}$ | MS |
|---|---|---|
| 133 | H | $MH^+$ 432 |
| 134 | $CH_3$ | $MH^+$ 446 |

EXAMPLE 135

3-(6-Chloro-3-dimethylaminomethyl-quinolin-5-yl)-4-(1H-indol-3-yl)-pyrrole-2,5-dione

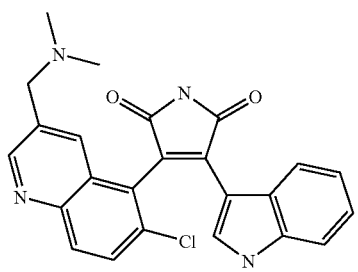

To a solution of 2-(6-chloro-3-dimethylaminomethyl-quinolin-5-yl)-acetamide (100 mg, 0.36 mmol) and (1H-indol-3-yl)-oxo-acetic acid methyl ester (110 mg, 0.54 mmol) in anhydrous THF was added dropwise a 1 M solution of t-BuOK in THF (1.8 mL) under an argon atmosphere at 0° C. The resulting deep red reaction mixture was stirred for 30 min. at 0° C., poured into a saturated aqueous NH$_4$Cl solution and extracted twice with EtOAc. The combined organic layers were washed with brine, dried over Na$_2$SO$_4$, filtered and concentrated at reduced pressure to afford an orange solid. Purification by size exclusion chromatography (Sephadex LH-20, MeOH afforded the title compound as an orange solid (88.3 mg, 0.205 mmol, 57%). $^1$H NMR (400 MHz, DMSO-d$_6$, 298 K): δ=11.88 (bs, 1H), 11.25 (bs, 1H), 8.69 (d, J=1.9 Hz, 1H), 8.10 (d, J=9.0 Hz, 1H), 8.02 (s, 1H), 7.91 (d, J=9.0 Hz, 1H), 7.85 (bs, 1H), 7.26 (d, J=8.1 Hz, 1H), 6.88 (t, J=7.4 Hz, 1H), 6.44 (t, J=7.4 Hz, 1H), 6.12 (d, J=8.1 Hz, 1H), 3.36 (AB-system: δA=3.48 (d, J$_{AB}$=−13.2 Hz, 1H), δB=3.25 (d, J$_{AB}$=−13.2 Hz, 1H)), 1.78 (s, 6H). MS (ES$^+$): 431 (M(C$_{24}$H$_{19}$$^{35}$ClN$_4$O$_2$)+H)$^+$.

Preparation of 2-(6-Chloro-3-dimethylaminomethyl-quinolin-5-yl)-acetamide

A solution of (6-chloro-3-dimethylaminomethyl-quinolin-5-yl)-acetic acid methyl ester (462 mg, 1.58 mmol) in a mixture of methanol (4 mL) and liquid ammonia (20 mL) was stirred for 4 days in an autoclave at room temperature. After careful evaporation of the ammonia, the remaining solvent was evaporated in vacuo to afford the title compound as a pale brown solid (413 mg, 1.48 mmol, 94%). $^1$H NMR (400 MHz, DMSO-d$_6$, 298 K): δ=8.85 (d, J=2.0 Hz, 1H), 8.31 (bs, 1H), 7.93 (d, J=9.1 Hz, 1H), 7.75 (d, J=9.1 Hz, 1H), 7.62 (bs, 1H), 7.08 (bs, 1H), 4.10 (s, 2H), 3.67 (bs, 2H), 2.23 (bs, 6H). MS (ES$^+$): 278 (M(C$_{14}$H$_{16}$$^{35}$ClN$_3$O)+H)$^+$.

Preparation of (6-Chloro-3-dimethylaminomethyl-quinolin-5-yl)-acetic acid methyl ester To a solution of (3-bromomethyl-6-chloro-quinolin-5-yl)-acetic acid methyl ester (500 mg, 1.52 mmol) in DMF (10 mL) was added a 33% solution of dimethylamine in ethanol (547 μL, 3.04 mmol). The reaction mixture was stirred for 16 h at room temperature, followed by removal of the solvents in vacuo. The residue was purified by flash column chromatography (silica gel, gradient of CH$_2$Cl$_2$/MeOH 100:0 to 90:10) to afford the title compound as a violet solid (424 mg, 1.45 mmol, 95%). %). $^1$H NMR (400 MHz, DMSO-d$_6$, 298 K): δ=8.89 (d, J=2.0 Hz, 1H), 8.38 (bs, 1H), 8.00 (d, J=9.1 Hz, 1H), 7.80 (d, J=9.1 Hz, 1H), 4.36 (s, 2H), 3.69 (bs, 2H), 3.63 (s, 3H), 2.24 (bs, 6H). MS (ES$^+$): 293 (M(C$_{15}$H$_7$$^{35}$ClN$_2$O$_2$)+H)$^+$.

Preparation of (3-Bromomethyl-6-chloro-quinolin-5-yl)-acetic acid methyl ester To a solution of (6-chloro-3-methyl-quinolin-5-yl)-acetic acid methyl ester (1.70 g, 6.81 mmol) in tetrachloromethane (140 mL) was added N-bromosuccinimide (1.28 g, 6.8 mmol). The reaction mixture was heated to 40° C. for 1 h under simultaneous irradiation by a 300 W UV lamp. The reaction mixture was filtered and the filtrate concentrated in vacuo. The crude product was purified by flash column chromatography (silica gel, gradient of cyclohexane/EtOAc 100:0 to 80:20) to afford the title compound as a white powder (1.34 g, 4.1 mmol, 60%). %). $^1$H NMR (400 MHz, CDCl$_3$, 298 K): δ=8.97 (s, 1H), 8.30 (s, 1H), 8.07 (d, J=9.0 Hz, 1H), 7.76 (d, J=9.0 Hz, 1H), 4.69 (s, 2H), 4.30 (s, 2H), 3.73 (s, 3H). MS (ES$^+$): 328 (M(Cl$_3$H$_{11}$$^{79}$Br$^{35}$ClNO$_2$)+H)$^+$.

Preparation of (6-Chloro-3-methyl-quinolin-5-yl)-acetic acid methyl ester

To a solution of 6-chloro-3-methyl-5-(2,2,2-trichloro-ethyl)quinoline (4.11 g, 13.3 mmol) in anhydrous methanol (35 mL) was added a 30% solution of NaOMe in methanol (10.7 mL) under an argon atmosphere. The resulting brown solution was heated for 4 h at 70° C. After cooling to 0° C., concentrated H$_2$SO$_4$ (7 mL) was carefully added and the resulting reaction mixture was heated for 1 h at 70° C. After cooling the reaction mixture was rendered basic (pH=9) with a saturated aqueous NaHCO$_3$ solution and extracted three times with TBDM. The combined organic layers were dried over Na$_2$SO$_4$, filtered and concentrated at reduced pressure to afford a brown solid. Purification by flash column chromatography (silica gel, gradient of cyclohexane/EtOAc 100:0 to 80:20) afforded the title compound as a white powder (2.22 g, 8.90 mmol, 67%). $^1$H NMR (400 MHz, CDCl$_3$, 298 K): δ=8.80 (s, 1H), 8.09 (s, 1H), 8.05 (d, J=9.2 Hz, 1H), 7.69 (d, J=9.2 Hz, 1H), 4.29 (s, 2H), 3.73 (s, 3H), 2.59 (s, 3H). MS (ES$^+$): 250 (M(C$_{13}$H$_{12}$$^{35}$ClNO$_2$)+H)$^+$.

Preparation of 6-Chloro-3-methyl-5-(2,2,2-trichloro-ethyl)quinoline

To a suspension of CuCl$_2$.2H$_2$O (5.23 g, 30.1 mmol) in acetonitrile (30 mL) was added t-butylnitrite (5.52 mL, 37.6 mmol) and 1,1-dichloroethene (30.7 mL, 376 mmol) at 0° C. under an argon atmosphere. After stirring for 5 minutes, a suspension of 6-chloro-3-methyl-5-aminoquinoline (4.82 g, 24.0 mmol) in acetonitrile (40 mL) was added dropwise at 0° C. The reaction mixture was stirred for 16 h at room temperature, followed by removal of the volatiles in vacuo. The residue was partitioned between a saturated aqueous NH$_4$Cl solution and TBDM. The layers were separated and the aqueous layer was extracted twice with TBDM. The combined organic layers were dried over Na$_2$SO$_4$, filtered and concentrated at reduced pressure to afford a brown solid. Purification by flash column chromatography (silica gel, gradient of cyclohexane/EtOAc 100:0 to 83:17) afforded the title compound as a violet solid ((4.11 g, 13.3 mmol, 53%). $^1$H NMR (400 MHz, CDCl$_3$, 298 K): δ=8.56 (s, 1H), 8.15 (s, 1H), 7.87 (d, J=9.0 Hz, 1H), 7.50 (d, J=9.0 Hz, 1H), 4.50 (s, 2H), 2.35 (s, 3H). MS (ES$^+$): 308 (M(C$_{12}$H$_9$$^{35}$Cl$_4$N)+H)$^+$.

Preparation of 6-Chloro-3-methyl-5-aminoquinoline

To a solution of 6-chloro-3-methyl-5-nitroquinoline (6.70 g, 30.1 mmol) in methanol (45 mL) was added iron powder (5.55 g, 99.3 mmol), followed by careful addition of a concentrated aqueous HCl solution (15.6 mL). The resulting reaction mixture was heated for 1 h at 50° C. and concentrated at reduced pressure using a rotary evaporator. The residue was dissolved in water and basified (pH=9) using a 33% aqueous ammonia solution. The resulting brown suspension was extracted twice with EtOAc and the combined organic layers were washed with brine, dried over Na$_2$SO$_4$, filtered and concentrated at reduced pressure to afford the title compound as a brown solid (4.92 g, 25.5 mmol, 85%). $^1$H NMR (400 MHz, CDCl$_3$, 298 K): δ=8.75 (s, 1H), 7.93 (s, 1H), 7.53 (d, J=9.0 Hz, 1H), 7.50 (d, J=9.0 Hz, 1H), 2.56 (s, 3H). MS (ES$^+$): 193 (M(C$_{10}$H$_9^{35}$ClN$_2$)+H)$^+$.

Preparation of 6-Chloro-3-methyl-5-nitroquinoline

To a solution of 6-chloro-3-methylquinoline (6.3 g, 35.6 mmol) in concentrated H$_2$SO$_4$ (22 mL) was added dropwise a solution of KNO$_3$ (3.77 g, 37.2 mmol) in concentrated H$_2$SO$_4$ (22 mL) at 0° C. Care was taken that the temperature of the reaction mixture did not rise above 10° C. The reaction mixture was stirred for 1 h at 0° C. and 12 h at room temperature. It was then poured onto ice (150 g) and rendered basic (pH=10) with a 33% aqueous ammonia solution. A dark yellow precipitate was formed, which was filtered off, thoroughly rinsed with water and dried in vacuo to afford the title compound as a brown solid (7.1 g, 31.9 mmol, 90%). $^1$H NMR (400 MHz, CDCl$_3$, 298 K): δ=8.89 (s, 1H), 8.20 (d, J=9.0 Hz, 1H), 7.82 (s, 1H), 7.72 (s, 1H), 2.59 (s, 3H). MS (ES$^+$): 223 (M(C$_{10}$H$_7^{35}$ClN$_2$O$_2$)+H)$^+$.

Preparation of 6-Chloro-3-methylquinoline

To a solution of 4-chloroaniline (9.59 g, 75.2 mmol) in dioxane (112 mL) was added a 6 M aqueous solution of HCl (180 mL). The reaction mixture was heated to 100° C. and a solution of 2-methyl-2-propene-1,1-diol acetate (15.5 g, 90.3 mmol) in dioxane (20 mL) was added dropwise during 1 h under an argon atmosphere. The reaction mixture was stirred for 2 h at 120° C. after which an aliquot was taken and analyzed by HPLC. Since some starting material was still left, the reaction mixture was cooled down to 100° C. and another portion of 2-methyl-2-propene-1,1-diol actetate (5.2 g, 30 mmol) was added during 1 h. After heating for 2 h at 120° C., the reaction mixture was cooled down again to 100° C. and a final portion of 2-methyl-2-propene-1,1-diol actetate (5.2 g, 30 mmol) was added during 1 h at 100° C. Heating was continued for 30 min. at 120° C. After cooling to ambient temperature the reaction mixture was diluted with water (100 mL) and extracted with 2-methoxy-2-methylpropane (2×200 mL). The combined organic phases were extracted with a 4 M HCl solution (100 mL). The combined aqueous phases were basified to pH 9 with a 4 M NaOH solution and extracted with TBME (3×200 mL). The combined organic layers were washed with brine (100 mL), dried over Na$_2$SO$_4$, filtered and concentrated at reduced pressure to afford a brown oil. The crude product was purified by flash column chromatography (silica gel, cyclohexane/EtOAc 95:5) to afford 6-chloro-3-methylquinoline as a pale brown crystalline solid (6.32 g, 35.6 mmol, 47%). $^1$H NMR (400 MHz, CDCl$_3$, 298 K): δ=8.78 (d, J=2.2 Hz, 1H), 8.03 (d, J=8.8 Hz, 1H), 7.86 (bs, 1H), 7.75 (d, J=2.2 Hz, 1H), 7.60 (dd, J=8.8 Hz, 2.2 Hz, 1H), 2.55 (s, 3H). MS (ES$^+$): 178 (M(C$_{10}$H$_8^{35}$ClN)+H)$^+$.

EXAMPLES 136-144

By following the procedures of Example 135, but by using the appropriate starting materials, the compounds of formula D wherein R$_a$, R$_b$, R$_3$, R$_4$ and X are as indicated in Table 4 below, and R$_c$ and R$_d$ is H, may be obtained.

TABLE 4

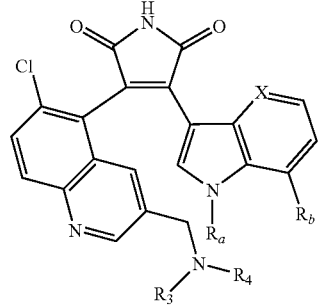

D

| | R$_3$ | R$_4$ | R$_a$ | R$_b$ | X | MS |
|---|---|---|---|---|---|---|
| 136. | CH$_3$ | CH$_3$ | H | CH$_3$ | CH | MH$^+$ 445 |
| 137. | CH$_3$ | CH$_3$ | CH$_3$ | H | H | MH$^+$ 445 |
| 138. | CH$_3$ | CH$_3$ | H | H | N | MH$^+$ 432 |
| 139. | H | —CH$_2$CHCH$_2$— | H | H | CH | MH$^+$ 443 |
| 140. | H | —CH$_2$CHCH$_2$— | H | CH$_3$ | CH | MH$^+$ 457 |
| 141. | H | —CH$_2$CHCH$_2$— | H | H | N | MH$^+$ 444 |
| 142. | CH$_2$CH$_2$CH$_2$CH$_2$ | | H | H | CH | MH$^+$ 457 |
| 143. | CH$_2$CH$_2$CH$_2$CH$_2$ | | H | CH$_3$ | CH | MH$^+$ 471 |
| 144. | CH$_2$CH$_2$CH$_2$CH$_2$ | | H | H | N | MH$^+$ 458 |

EXAMPLE 145

3-(6-Chloro-3-dimethylaminomethyl-isoquinolin-5-yl)-4-(1-methyl-1H-indol-3-yl)-pyrrole-2,5-dione

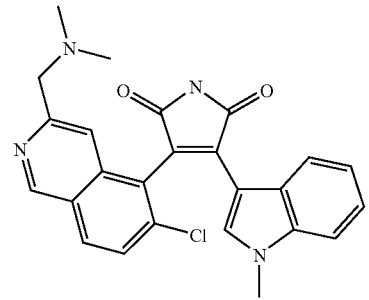

To a solution of 2-(6-chloro-3-dimethylaminomethyl-isoquinolin-5-yl)-acetamide (47 mg, 0.17 mmol) and (1-methyl-1H-indol-3-yl)-oxo-acetic acid methyl ester (56 mg, 0.26 mmol) in anhydrous THF was added dropwise a 1 M solution of potassium t-BuOK in THF (1.8 mL) under an argon atmosphere at 0° C. The resulting deep red reaction mixture was stirred for 1.5 h at 0° C., quenched with a saturated aqueous NH$_4$Cl solution and extracted twice with EtOAc. The combined organic layers were washed with brine, dried over Na$_2$SO$_4$, filtered and concentrated at reduced pressure. Purification by flash column chromatography (silica gel, EtOAc/water/acetic acid 7:1:1) afforded the title compound as its acetate salt (61 mg, 0.12 mmol, 70%). MS (ES$^+$): 445 (M(C$_{25}$H$_{21}^{35}$ClN$_4$O$_2$)+H)$^+$.

Preparation of 2-(6-Chloro-3-dimethylaminomethyl-isoquinolin-5-yl)-acetamide

A solution of (6-chloro-3-dimethylaminomethyl-isoquinolin-5-yl)-acetic acid methyl ester (515 mg, 1.76 mmol)

in a mixture of methanol (10 mL) and liquid ammonia (10 mL) was stirred for 16 h in an autoclave at 70° C. After careful evaporation of the ammonia, the remaining solvent was evaporated in vacuo to afford the title compound as a brown solid (410 mg, 1.48 mmol, 84%). MS (ES$^+$): 278 (M($C_{14}H_{16}{}^{35}ClN_3O$)+H)$^+$.

Preparation of (6-Chloro-3-dimethylaminomethyl-isoquinolin-5-yl)-acetic acid methyl ester To a solution of (3-bromomethyl-6-chloro-isoquinolin-5-yl)-acetic acid methyl ester (500 mg, 1.52 mmol) in THF (50 mL) was added a 50% solution of dimethylamine in THF (20 mL). The reaction mixture was stirred for 30 min. at room temperature, followed by removal of the solvents in vacuo. The residue was purified by flash column chromatography (silica gel, gradient of $CH_2Cl_2$/MeOH 100:0 to 95:5) to afford the title compound as a yellow oil (445 mg, 1.52 mmol, 100%). MS (ES$^+$): 293 (M($C_{15}H_{17}{}^{35}ClN_2O_2$)+H)$^+$.

Preparation of (3-Bromomethyl-6-chloro-isoquinolin-5-yl)-acetic acid methyl ester To a solution of (6-Chloro-3-methyl-isoquinolin-5-yl)-acetic acid methyl ester (1.9 g, 7.63 mmol) in tetrachloromethane (190 mL) was added N-bromosuccinimide (1.36 g, 7.63 mmol). The reaction mixture was heated to 40° C. for 1 h under simultaneous irradiation by a 300 W UV lamp, filtered and the filtrate concentrated in vacuo. The crude product was purified by flash column chromatography (silica gel, cyclohexane/EtOAc 80:20) to afford the title compound as a white powder (1.00 g, 3.05 mmol, 40%). MS (ES$^+$): 328 (M($C_{13}H_{11}{}^{79}Br^{35}ClNO_2$)+H)$^+$.

Preparation of (6-Chloro-3-methyl-isoquinolin-5-yl)-acetic acid methyl ester

To a solution of 6-chloro-3-methyl-5-(2,2,2-trichloro-ethyl)isoquinoline (3.3 g, 10.7 mmol) in anhydrous methanol (64 mL) was added a 30% solution of NaOMe in methanol (9.6 mL) under an argon atmosphere. The resulting brown solution was heated for 3 h at 70° C. After cooling to 0° C., concentrated $H_2SO_4$ (5.7 mL) was carefully added and the resulting reaction mixture was heated for 1 h at 70° C. After cooling the reaction mixture was rendered basic (pH=9) with a saturated aqueous $NaHCO_3$ solution and extracted three times with diethyl ether. The combined organic layers were dried over $Na_2SO_4$, filtered and concentrated at reduced pressure to afford a brown solid. Purification by flash column chromatography (silica gel, cyclohexane/ethyl actetate 70:30) afforded the title compound as a brown powder (1.91 g, 7.63 mmol, 70%). MS (ES$^+$): 250 (M($C_{13}H_{12}{}^{35}ClNO_2$)+H)$^+$.

Preparation of 6-Chloro-3-methyl-5-(2,2-trichloro-ethyl)-isoquinoline

To a suspension of $CuCl_2 \cdot 2H_2O$ (5.96 g, 35.0 mmol) in acetonitrile (175 mL) was added t-butylnitrite (5.97 mL, 43.7 mmol) and 1,1-dichloroethene (35.0 mL, 437 mmol) at 0° C. under an argon atmosphere. After stirring for 5 minutes, a suspension of 6-chloro-3-methyl-5-aminoisoquinoline (5.62 g, 29.2 mmol) in acetonitrile (175 mL) was added dropwise at 0° C. The reaction mixture was stirred for 16 h at room temperature, followed by removal of the volatiles in vacuo. The residue was partitioned between a saturated $NH_4Cl$ solution and EtOAc. The layers were separated and the aqueous layer was extracted twice with EtOAc. The combined organic layers were dried over $Na_2SO_4$, filtered and concentrated at reduced pressure to afford a brown solid. Purification by flash column chromatography (silica gel, cyclohexane/EtOAc 50:50) afforded the title compound as a dark yellow powder ((3.3 g, 10.7 mmol, 37%). MS (ES$^+$): 308 (M($C_{12}H_9{}^{35}Cl_4N$)+H)$^+$.

Preparation of 6-Chloro-3-methyl-5-aminoisoquinoline

To a solution of 6-chloro-3-methyl-5-nitroisoquinoline (8.00 g, 36 mmol) in methanol (200 mL) was added iron powder (6.68 g, 119 mmol), followed by careful addition of a concentrated aqueous HCl solution (18 mL). The resulting reaction mixture was heated for 1 h at 50° C. and concentrated at reduced pressure using a rotary evaporator. The residue was dissolved in water and basified (pH=9) using a 25% aqueous ammonia solution. The resulting brown suspension was extracted twice with ethyl acetate and the combined organic layers were washed with brine, dried over $Na_2SO_4$, filtered and concentrated at reduced pressure to afford the title compound as a brown solid (6.09 g, 31.6 mmol, 88%). MS (ES$^+$): 193 (M($C_{10}H_9{}^{35}ClN_2$)+H)$^+$.

Preparation of 6-Chloro-3-methyl-5-nitroisoquinoline

To a solution of 6-chloro-3-methylisoquinoline (10.0 g, 57.5 mmol) in concentrated $H_2SO_4$ (100 mL) was added dropwise during 10 min. a solution of $KNO_3$ (6.05 g, 60 mmol) in concentrated $H_2SO_4$ (50 mL) at 5° C. Care was taken that the temperature of the reaction mixture did not rise above 10° C. The reaction mixture was stirred for 3 h at room temperature, poured onto ice (200 g) and rendered basic (pH=10) with a 33% aqueous ammonia solution. A dark yellow precipitate was formed, which was filtered off, thoroughly rinsed with water and taken up in dichloromethane. The organic phase was washed with water and brine, dried over $Na_2SO_4$, filtered and dried in vacuo to afford a pale brown solid. Re-crystallization from dichloromethane/pentane afforded the title compound as pale brown crystals (9.2, 41.4 mmol, 72%). MS (ES$^+$): 223 (M($C_{10}H_7{}^{35}ClN_2O_2$)+H)$^+$.

Preparation of 6-Chloro-3-methylisoquinoline

During 10 min. (4-chloro-benzyl)-[2,2-dimethoxy-1-methyl-eth-(Z)-ylidene]-amine (120 g, 0.496 mol) was added dropwise to polyphosphoric acid (1000 g) at 130° C. The resulting reaction mixture was heated for 3 h at 140° C. After cooling below 100° C. the reaction mixture was poured onto ice (1 kg) and neutralized (pH=7) with a 33% aqueous NaOH solution. Care was taken that the temperature did not rise above 35° C. by adding additional ice. The reaction mixture was extracted with dichloromethane (3×1 L) and the combined organic layers were dried over $Na_2SO_4$, filtered and concentrated at reduced pressure to afford a black oil. The crude product was purified bulb-to-bulb distillation (105-110° C., 2 mbar) to afford the title compound as colorless oil which crystallized upon standing (66.7 g, 0.375 mol, 76%). MS (ES$^+$): 178 (M($C_{10}H_8{}^{35}ClN$)+H)$^+$.

Preparation of (4-Chloro-benzyl)-[2,2-dimethoxy-1-methyl-eth-(Z)-ylidene]-amine

In a three-necked round bottomed flask equipped with a Dean Stark trap and reflux cooler, a solution of 4-chlorobenzylamine (97.3 g, 0.687 mol) and 1,1-dimethoxy-propan-2-one (89.5 g, 0.758 mol) in toluene (300 mL) was heated for 3 h at reflux. The reaction mixture was cooled down and the solvent removed in vacuo to yield the title compound as a pale yellow oil (166 g, 0.687 mol, 100%). MS (ES$^+$): 242 $(M(C_{12}H_{16}{}^{35}ClNO_2)+H)^+$.MS (ES$^+$): 242 (M+H)$^+$.

EXAMPLES 146-150

By following the procedures of Example 145, but by using the appropriate starting materials, the compounds of formula E wherein $R_a$, $R_b$, $R_3$, $R_4$ and X are as indicated in Table 5 below, and $R_r$ and $R_d$ is H, may be obtained.

TABLE 5

E

| | $R_3$ | $R_4$ | $R_a$ | $R_b$ | X | MS |
|---|---|---|---|---|---|---|
| 146. | CH$_3$ | CH$_3$ | H | H | CH | MH$^+$ 431 |
| 147. | CH$_3$ | CH$_3$ | H | H | N | MH$^+$ 432 |
| 148. | H | —CH$_2$CHCH$_2$— | H | H | CH | MH$^+$ 443 |
| 149. | CH$_2$CH$_2$CH$_2$CH$_3$ | | H | H | CH | MH$^+$ 457 |
| 150. | H | —CH$_2$CHCH$_2$— | H | CH$_3$ | CH | MH$^+$ 457 |

EXAMPLE 151

3-(7-Chloro-2-dimethylaminomethyl-quinolin-8-yl)-4-(7-methyl-1H-indol-3-yl)-pyrrole-2,5-dione

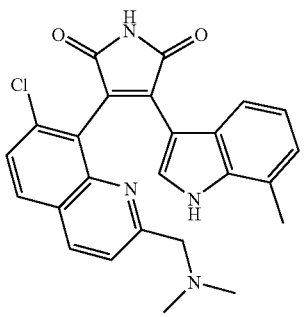

Potassium tert-butoxide (1.0 M in THF, 0.60 ml, 0.60 mmol, 3.0 equiv) was added at room temperature under an atmosphere of argon to a solution of (7-methyl-1H-indol-3-yl)-oxo-acetic acid methyl ester (65 mg, 0.30 mmol, 1.5 equiv) and of 2-(7-chloro-2-dimethylaminomethyl-quinolin-8-yl)-acetamide (55 mg, 0.20 mmol) in anhydrous tetrahydrofuran (2.0 ml, dried over molecular sieves). The reaction mixture was stirred for 15 minutes at room temperature. It was then diluted with EtOAc and poured into a saturated aqueous NH$_4$Cl solution. After three extractions with EtOAc, the combined organic layers were dried over Na$_2$SO$_4$, filtered and concentrated in vacuo. Purification of the residue via preparative HPLC afforded the title compound (64 mg, 58%) as its trifluoroacetate salt. $^1$H NMR (400 MHz, d$_6$-DMSO): δ=11.90 (br s, 1H), 11.18 (s, 1H), 9.72 (br s, 1H), 8.59 (d, J=8.2 Hz, 1H), 8.19 (d, J=9.2 Hz, 1H), 7.98 (d, J=2.6 Hz, 1H), 7.77 (d, J=8.8 Hz, 1H), 7.61 (d, J=8.8 Hz, 1H), 6.73 (d, J=7.3 Hz, 1H), 6.33 (t, J=7.3 Hz, 1H), 5.94 (d, J=7.3 Hz, 1H), 4.59 (s, 2H), 2.69 (br s, 6H), 2.38 (s, 3H). MS (ES$^+$): 445.3 (M+H)$^+$.

Preparation of 2-(7-Chloro-2-dimethylaminomethyl-quinolin-8-yl)-acetamide

Formamide (118 mg, 2.62 mmol, 3.35 equiv) was added to a solution of (7-chloro-2-dimethylaminomethyl-quinolin-8-yl)-acetic acid ethyl ester (240 mg, 0.78 mmol) in N,N-dimethylformamide (1.0 ml). The solution was heated to 105° C., and then sodium methoxide (5.4 M in MeOH, 0.14 ml, 0.78 mmol, 1.0 equiv) was added dropwise over 20 minutes. After 1 hour, the reaction mixture was cooled to room temperature, diluted with water, and extracted with EtOAc and CH$_2$Cl$_2$. The combined organic layers were washed with brine, dried over Na$_2$SO$_4$, filtered, and concentrated in vacuo. Purification of the residue via flash chromatrography (gradient of CH$_2$Cl$_2$/MeOH 96:4 to 60:40) afforded the title compound (161 mg, 74%) as a white solid. $^1$H NMR (400 MHz, d$_6$-DMSO): δ=8.35 (d, J=8.9 Hz, 1H), 7.89 (d, J=9.2 Hz, 1H), 7.63 (d, J=9.2 Hz, 1H), 7.60 (d, J=8.9 Hz, 1H), 7.41 (br s, 1H), 6.88 (br s, 1H), 4.26 (s, 2H), 3.69 (s, 2H), 2.21 (s, 6H). MS (ES$^+$): 278.3 (M+H)$^+$.

Preparation of (7-Chloro-2-dimethylaminomethyl-quinolin-8-yl)-acetic acid ethyl ester Dimethylamine (5.6 M solution in EtOH, 0.27 ml, 1.54 mmol, 1.5 equiv) was added to a solution of (7-chloro-2-formyl-quinolin-8-yl)-acetic acid ethyl ester (285 mg, 1.03 mmol) in anhydrous THF (5 ml). The reaction mixture was stirred at room temperature for 18 hours. A solution of NaCNBH$_3$ (77 mg, 1.23 mmol, 1.2 equiv) in methanol (2 ml) was added, immediately followed by the addition of acetic acid (308 mg, 5.13 mmol, 5.0 equiv). After 5 minutes at room temperature, TLC analysis indicated complete conversion. The reaction mixture was diluted with water, adjusted to pH=8 with concentrated aqueous NaHCO$_3$ solution, and extracted with EtOAc. The combined organic layers were washed with brine, dried over Na$_2$SO$_4$, filtered and concentrated in vacuo. The residue was purified via flash chromatography (gradient of CH$_2$Cl$_2$/MeOH 99:1 to 90:10) to afford the title compound (245 mg, 78%) as a colorless solid. $^1$H NMR (400 MHz, d$_6$-DMSO): δ=8.45 (d, J=8.1 Hz, 1H), 7.98 (d, J=8.4 Hz, 1H), 7.69 (d, J=8.4 Hz, 1H), 7.63 (d, J=8.1 Hz, 1H), 4.47 (s, 2H), 4.08 (q, J=7.3 Hz, 2H), 2.50 (s, 6H), 1.16 (t, J=7.3 Hz, 3H). MS (ES$^+$): 307.3 (M+H)$^+$.

Preparation of (7-Chloro-2-formyl-quinolin-8-yl)-acetic acid ethyl ester

Selenious acid (193 mg, 1.50 mmol, 1.1 equiv) was added to a solution of (7-chloro-2-methyl-quinolin-8-yl)-acetic acid ethyl ester in dioxane (12 ml). The reaction mixture was heated to 100° C. After 20 and 40 minutes, additional portions of selenious acid (88 mg each) were added, and heating was continued for a total of 90 minutes. After cooling, the reaction mixture was diluted with water, filtered, and extracted with EtOAc. The combined organic layers were washed with brine, dried over $Na_2SO_4$, filtered, and concentrated in vacuo. The residue was purified via flash chromatography (gradient of hexane/EtOAc 100:0 to 80:20) to afford the title compound (292 mg, 77%). $^1H$ NMR (400 MHz, $CDCl_3$): δ=10.18 (s, 1H), 8.31 (d, J=8.1 Hz, 1H), 8.04 (d, J=8.1 Hz, 1H), 7.82 (d, J=7.7 Hz, 1H), 7.71 (d, J=7.7 Hz, 1H), 4.61 (s, 2H), 4.22 (q, J=7.3 Hz, 2H), 1.28 (t, J=7.3 Hz, 3H). MS ($ES^+$): 278.2 $(M+H)^+$.

Preparation of
(7-Chloro-2-methyl-quinolin-8-yl)-acetic acid ethyl ester (7-Chloro-2-methyl-quinolin-8-yl)-acetic acid tert-butyl ester (650 mg, 2.23 mmol) was dissolved in ethanol (13 ml) saturated with HCl gas. The solution was heated to 90° C. for 10 minutes. After cooling, volatiles were removed in vacuo, and the residue was purified via flash chromatography (gradient of hexane: EtOAc 95:5 to 80:20) to afford the title compound (372 mg, 63%) as a yellow solid. $^1H$ NMR (400 MHz, $CDCl_3$): δ=8.00 (d, J=8.8 Hz, 1H), 7.66 (d, J=8.8 Hz, 1H), 7.48 (d, J=9.2 Hz, 1H), 7.27 (d, J=8.8 Hz, 1H); 4.52 (s, 2H), 4.19 (q, J=7.3 Hz, 2H), 2.81 (s, 3H), 1.27 (t, J=7.3 Hz, 3H). MS ($ES^+$): 264.2 $(M+H)^+$.

Preparation of
(7-Chloro-2-methyl-quinolin-8-yl)-acetic acid tert-butyl ester n-Butyl lithium (1.6 M in hexane, 5.3 ml, 8.52 mmol, 1.5 equiv) was added at −78° C. under an atmosphere of argon to a degassed solution of hexamethyl disilazide (1.38 g, 8.52 mmol, 1.5 equiv) in toluene (16 ml). After stirring at −78° C. for 15 minutes and at room temperature for 15 minutes, $Pd_2(dba)_3$ (156 mg, 0.17 mmol, 0.03 equiv) and (2'-dicyclohexylphosphanyl-biphenyl-2-yl)-dimethyl-amine (141 mg, 0.36 mmol, 0.063 equiv) were added. After stirring at room temperature for 10 minutes, the reaction mixture was cooled to −10° C. and treated dropwise with acetic acid tert-butyl ester (858 mg, 7.38 mmol, 1.3 equiv). After stirring for 10 minutes at −10° C., trifluoro-methanesulfonic acid 7-chloro-2-methyl-quinolin-8-yl ester (1.85 g, 5.68 mmol) was added in one portion, and the cooling bath was removed. The temperature of the reaction mixture rose to 29° C. within the next 30 minutes. After 40 minutes, TLC analysis indicated formation of unwanted side products (e.g. 4-(7-chloro-2-methyl-quinolin-8-yl)-3-oxo-butyric acid tert-butyl ester). The reaction mixture was diluted with water, filtered, and extracted with EtOAc. The combined organic layers were washed with brine, dried over $Na_2SO_4$, filtered and concentrated in vacuo. The residue was purified via flash chromatography (gradient of toluene/EtOAc 100:0 to 95:5) to afford the title compound (662 mg, 40%) as a yellow oil. $^1H$ NMR (400 MHz, $CDCl_3$): δ=7.98 (d, J=12.8 Hz, 1H), 7.63 (d, J=12.8 Hz, 1H), 7.47 (d, J=12.8 Hz, 1H), 7.26 (d, J=12.8 Hz, 1H), 4.43 (s, 2H), 2.72 (s, 3H), 1.47 (s, 9H). MS ($ES^+$): 292.2 $(M+H)^+$.

Preparation of Trifluoro-methanesulfonic acid 7-chloro-2-methyl-quinolin-8-yl ester 2,6-Lutidine (4.43 g, 41.32 mmol, 2.5 equiv) were added at room temperature under an atmosphere of argon to a solution of 7-chloro-2-methyl-quinolin-8-ol (3.20 g, 16.53 mmol) in anhydrous $CH_2Cl_2$ (65 ml). At 0° C., trifluoromethanesulfonic anhydride (5.60 g, 19.83 mmol, 1.2 equiv) was added dropwise, and the resulting solution was stirred at 0° C. for 10 minutes. The reaction mixture was diluted with water, and the aqueous phase was extracted with EtOAc. The combined organic layers were washed with brine, dried over $Na_2SO_4$, filtered and concentrated in vacuo. The residue was purified via flash chromatography (gradient of hexane/EtOAc 100:0 to 80:20) to afford the title compound (1.86 g, 35%). $^1H$ NMR (400 MHz, $CDCl_3$): δ=8.05 (d, J=8.6 Hz, 1H), 7.71 (d, J=8.7 Hz, 1H), 7.52 (d, J=8.9 Hz, 1H), 7.38 (d, J=8.5 Hz, 1H), 2.78 (s, 3H). MS ($ES^+$): 326 $(M+H)^+$.

Preparation of 7-Chloro-2-methyl-quinolin-8-ol

7-Chloro-8-hydroxy-2-methyl-quinoline-5-sulfonic acid (5.50 g, 20.09 mmol) was dissolved in acetic acid (30 ml) and sulfuric acid (3 ml), and the resulting solution was heated to 130° C. for 72 hours. Upon cooling, the reaction mixture was diluted with water (300 ml) and neutralized by the addition of solid $NaHCO_3$. The aqueous phase was extracted with EtOAc. The combined organic layers were washed with brine, dried over $Na_2SO_4$, filtered and concentrated in vacuo. The residue was purified via flash chromatography (gradient of hexane/EtOAc 95:5 to 70:30) to afford the title compound (3.20 g, 82%) as a yellow solid. $^1H$ NMR (400 MHz, $d_6$-DMSO): δ=10.6-10.1 (br, 1H), 8.30 (d, J=7.7 Hz, 1H), 7.55-7.51 (m, 2H), 7.43 (d, J=8.8 Hz, 1H), 2.77 (s, 3H). MS ($ES^-$): 192.2 $(M-H)^-$.

Preparation of
7-Chloro-8-hydroxy-2-methyl-quinoline-5-sulfonic acid

8-Hydroxy-2-methyl-quinoline-5-sulfonic acid (14.0 g, 58.52 mmol) was added to a solution of potassium hydroxide (9.20 g, 164 mmol, 2.8 equiv) in water (136 ml) to form a yellow solution. An aqueous solution of sodium hypochlorite (13%, 136 ml) was added. The mixture was stirred at room temperature for 90 minutes. Upon dilution with water (300 ml), the mixture was filtered through amberlite IR-120 ($H^+$). After washing the column with water (2 liters), the eluent was concentrated (to ~200 ml) and diluted with acetone (300 ml). The precipitate was filtered off and washed with acetone to afford the title compound (5.51 g, 34%). $^1H$ NMR (400 MHz, $d_6$-DMSO): δ=8.52 (d, J=8.3 Hz, 1H), 7.67 (d, J=8.3 Hz, 1H), 7.00 (s, 1H), 2.58 (s, 3H). MS ($ES^-$): 274 $(M-H)^-$.

Preparation of
8-Hydroxy-2-methyl-quinoline-5-sulfonic acid

Oleum (18-24% $SO_3$, 20 ml) was added to a solution of 2-methyl-quinolin-8-ol (10 g, 62.8 mmol) in concentrated sulfuric acid (40 ml). After warming to 65° C. for 2 hours, the reaction mixture was poured onto 200 g of crushed ice. The suspension was diluted with acetone (60 ml) and stirred for 10 minutes, whereupon solids were filtered off. After washing with acetone (3×60 ml) and drying under high vacuum, the title compound (14.13 g, 94%) was obtained as a slightly yellowish solid. $^1H$ NMR (400 MHz, $d_6$-DMSO): δ=9.60 (d, J=8.3 Hz, 1H), 8.02-7.94 (m, 2H), 7.29 (d, J=7.7 Hz, 1H), 2.94 (s, 3H). MS ($ES^+$): 240.2 $(M+H)^+$.

EXAMPLES 152-164

By following the procedures of Example 151, but by using the appropriate starting materials, the compounds of formula F wherein $R_a$, $R_b$, $R_1$, $R_2$ and $R_3$, are as indicated in Table 6 below, and $R_c$, $R_d$, and $R_e$ is H, may be obtained

TABLE 6

F

| | $R_1$ | $R_2$ | $R_3$ | $R_a$ | $R_b$ | MS |
|---|---|---|---|---|---|---|
| 152. | H | Cl | —CH$_2$N(CH$_3$)$_2$ | CH$_3$ | H | MH$^+$ 445 |
| 153. | Cl | Cl | —CH$_2$N(CH$_3$)$_2$ | CH$_3$ | H | MH$^+$ 480 |
| 154. | H | Cl | —CH$_2$N(CH$_3$)$_2$ | H | H | MH$^+$ 431 |
| 155. | OH | H | —CH$_2$N(CH$_3$)$_2$ | CH$_3$ | H | MH$^+$ 461 |
| 156. | Cl | Cl | —CH$_2$N(CH$_3$)$_2$ | H | H | MH$^+$ 466 |
| 157. | H | Cl | —CH$_2$N(CH$_3$)$_2$ | H | CH$_3$ | MH$^+$ 445 |
| 158. | OH | Cl | —CH$_2$N(CH$_3$)$_2$ | H | CH$_3$ | MH$^+$ 461 |
| 159. | Cl | Cl | —CH$_2$N(CH$_3$)$_2$ | H | CH$_3$ | MH$^+$ 480 |
| 160. | OH | H | —CH$_2$N(CH$_3$)$_2$ | CH$_3$ | H | MH$^+$ 427 |
| 161. | OH | H | —CH$_2$N(CH$_3$)$_2$ | H | H | MH$^+$ 413 |
| 162. | Cl | H | —CH$_2$N(CH$_3$)$_2$ | H | H | MH$^+$ 431 |
| 163. | Cl | H | —CH$_2$N(CH$_3$)$_2$ | CH$_3$ | H | MH$^+$ 445 |
| 164. | H | H | —CH$_2$N(CH$_3$)$_2$ | H | CH$_3$ | MH$^+$ 411 |

EXAMPLE 165

3-(6-chloro-3-dimethylaminomethyl-quinoxalin-5-yl)-4-(1H-indol-3-yl)-pyrrole-2,5-dione

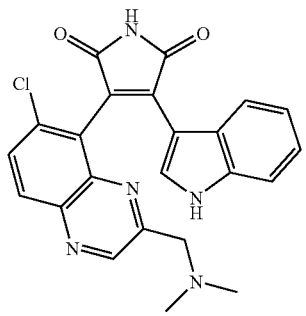

Potassium tert-butoxide (1.0 M in THF, 0.86 ml, 0.86 mmol, 4.0 equiv) was added at room temperature under an atmosphere of argon to a solution of (1H-indol-3-yl)-oxo-acetic acid methyl ester (66 mg, 0.32 mmol, 1.5 equiv) and of 2-(6-chloro-3-dimethylaminomethyl-quinoxalin-5-yl)-acetamide (60 mg, 0.22 mmol) in anhydrous tetrahydrofuran (3.0 ml, dried over molecular sieves). The reaction mixture was stirred for 15 minutes at room temperature. It was then diluted with EtOAc and poured into a saturated aqueous NH$_4$Cl solution. After three extractions with EtOAc, the combined organic layers were dried over Na$_2$SO$_4$, filtered and concentrated in vacuo. Purification of the residue via preparative HPLC afforded the title compound (32 mg, 27%) and 3-(3-dimethylaminomethyl-6-hydroxy-quinoxalin-5-yl)-4-(1H-indol-3-yl)-pyrrole-2,5-dione (14 mg, 12%) as their trifluoroacetate salts. Data for 3-(6-chloro-3-dimethylaminomethyl-quinoxalin-5-yl)-4-(1H-indol-3-yl)-pyrrole-2,5-dione:

$^1$H NMR (400 MHz, d$_6$-DMSO): δ=11.97 (s, 1H), 11.26 (s, 1H), 9.86 (s, 1H), 9.01 (s, 1H) 8.29 (d, J=9.0 Hz, 1H), 8.06-8.04 (m, 2H), 7.35 (d, J=8.0 Hz, 1H), 6.96 (dt, J=7.6/1.0 Hz, 1H), 6.49 (dt, J=8.1/1.0 Hz, 1H), 6.09 (d, J=8.3 Hz, 1H), 4.68 (s, 2H), 2.66 (s, 6H). MS (ES$^+$): 432.2 (M+H)$^+$. Data for 3-(3-dimethylaminomethyl-6-hydroxy-quinoxalin-5-yl)-4-(1H-indol-3-yl)-pyrrole-2,5-dione: $^1$H NMR (400 MHz, d$_6$-DMSO): δ=11.80 (s, 1H), 11.01 (s, 1H), 10.64 (s, 1H), 9.79 (s, 1H), 8.75 (s, 1H), 8.08 (d, J=9.3 Hz, 1H), 7.95 (d, J=2.9 Hz, 1H), 7.51 (d, J=9.0 Hz, 1H), 7.32 (d, J=8.1 Hz, 1H), 6.93 (dt, J=7.6/0.9 Hz, 1H), 6.48 (dt, J=8.1/1.0 Hz, 1H), 6.34 (d, J=8.3 Hz), 4.58 (s, 2H), 2.67 (s, 6H). MS (ES$^+$): 414.3 (M+H)$^+$.

Preparation of 2-(6-Chloro-3-dimethylaminomethyl-quinoxalin-5-yl)-acetamide

A solution of lithium hydroxide (28 mg, 1.16 mmol, 1.2 equiv) in water (2 ml) was added to a solution of (6-chloro-3-dimethylaminomethyl-quinoxalin-5-yl)-acetic acid methyl ester (283 mg, 0.96 mmol) in dioxane (6 ml). After 1 hour at 50° C., another portion of lithium hydroxide (28 mg in 1 ml of water) was added, and heating to 50° C. was continued for another hour. Volatiles were removed in vacuo, and the residue was directly used in the next step. MS (ES$^+$): 280.2 (M+H)$^+$.

Hydrochloric acid (4 M in dioxane, 8 drops) was added to a solution of the above (6-chloro-3-dimethylaminomethyl-quinoxalin-5-yl)-acetic acid in N,N-dimethylformamide (3 ml). A solution of carbonyl diimidazole (188 mg, 1.16 mmol, 1.2 equiv) in N,N-dimethylformamide (5 ml) was added, and the mixture was stirred at room temperature for 1 hour. Concentrated aqueous ammonia (25%, 10 ml) was added, and after 10 minutes at room temperature, volatiles were removed in vacuo. The residue was purified via flash chromatorgraphy (gradient of CH$_2$Cl$_2$/MeOH 95:5 to 70:30) to afford the title compound (180 mg, 67%) as a foam. $^1$H NMR (400 MHz, d$_6$-DMSO): δ=9.02 (s, 1H), 8.06 (d, J=9.2 Hz, 1H), 7.94 (d, J=9.2 Hz, 1H), 7.54 (br s, 1H), 6.98 (br s, 1H), 4.7-4.5 (br, 2H), 4.32 (s, 2H), 2.78 (br s, 6H). MS (ES$^+$): 279.2 (M+H)$^+$.

Preparation of (6-Chloro-3-dimethylaminomethyl-quinoxalin-5-yl)-acetic acid methyl ester Dimethylamine (5.6 M solution in EtOH, 1.0 ml, 5.6 mmol, 1.5 equiv) was added to a solution of (6-chloro-3-formyl-quinoxalin-5-yl)-acetic acid methyl ester (966 mg, 3.65 mmol) in anhydrous THF (23 ml). The reaction mixture was stirred at room temperature for 18 hours. A solution of NaCNBH$_3$ (275 mg, 4.37 mmol, 1.2 equiv) in methanol (6 ml) was added, immediately followed by the addition of acetic acid (1.10 g, 18.25 mmol, 5.0 equiv). After 5 minutes at room temperature, TLC analysis indicated complete conversion. The reaction mixture was diluted with water, adjusted to pH=8 with concentrated aqueous NaHCO$_3$ solution, and extracted with EtOAc. The combined organic layers were washed with brine, dried over Na$_2$SO$_4$, filtered and concentrated in vacuo. The residue was purified via flash chromatography (gradient of CH$_2$Cl$_2$/MeOH 99:1 to 90:10) to afford the title compound (303 mg, 28%) as a colorless solid and the regioisomeric (6-chloro-2-dimethylaminomethyl-quinoxalin-5-yl)-acetic acid methyl ester (48 mg, 5%). Data for (6-chloro-3-dimethylaminomethyl-quinoxalin-5-yl)-acetic acid methyl ester: $^1$H NMR (400 MHz, CDCl$_3$): δ=9.13 (s, 1H), 8.02 (d, J=9.0 Hz, 1H), 7.81 (d, J=9.0 Hz, 1H), 4.52 (s, 2H), 4.39 (s, 2H), 3.68 (s, 3H), 2.80 (s, 6H). MS (ES$^+$): 294.2 (M+H)$^+$. Data for (6-chloro-2-dimethylaminomethyl-quinoxalin-5-yl)-acetic acid methyl ester: $^1$H NMR (400 MHz, CDCl$_3$): δ=9.30 (s, 1H), 7.98 (d, J=9.0 Hz, 1H), 7.84 (d, J=9.0 Hz, 1H), 4.49 (s, 2H), 3.82 (s, 2H), 3.71 (s, 3H), 2.34 (s, 6H). MS (ES$^+$): 294.2 (M+H)$^+$.

Preparation of (6-Chloro-3-formyl-quinoxalin-5-yl)-acetic acid methyl ester

Selenious acid (645 mg, 5.00 mmol, 1.1 equiv) was added to a solution of (6-chloro-3-methyl-quinoxalin-5-yl)-acetic acid methyl ester in dioxane (30 ml). The reaction mixture was heated to 100° C. After 60 minutes, an additional portion of selenious acid (645 mg) was added, and heating was continued for another 60 minutes. After cooling, the reaction mixture was diluted with water, filtered, and extracted with EtOAc. The combined organic layers were washed with brine, dried over Na$_2$SO$_4$, filtered, and concentrated in vacuo. The residue was purified via flash chromatography (gradient of hexane/EtOAc 100:0 to 80:20) to afford the title compound (966 mg, 81%). MS (ES$^+$): 264 (M+H)$^+$.

Preparation of (6-Chloro-3-methyl-quinoxalin-5-yl)-acetic acid methyl ester

NaOMe (5.4 M in MeOH, 8.3 ml, 44.71 mmol, 4.5 equiv) was added at room temperature to a solution of 7-chloro-2-methyl-8-(2,2,2-trichloro-ethyl)-quinoxaline (3.08 g, 9.94 mmol) in methanol (24 ml). The reaction mixture was heated to 70° C. for 3 hours. After cooling to 0° C., sulfuric acid (4.7 ml) dissolved in methanol (20 ml) was added, and the reaction mixture was heated to 70° C. for one hour. After cooling and dilution with EtOAc and H$_2$O, the mixture was filtered and extracted with EtOAc. The combined organic layers were washed with brine, dried over Na$_2$SO$_4$, filtered and concentrated in vacuo. The residue was purified via flash chromatography (gradient of hexane/EtOAc 100:0 to 70:30) to afford the title compound (1.14 g, 46%) as a solid. $^1$H NMR (400 MHz, CDCl$_3$): δ=8.70 (s, 1H), 7.95 (d, J=9.1 Hz, 1H), 7.69 (d, J=9.1 Hz, 1H), 4.48 (s, 2H), 3.70 (s, 3H), 2.74 (s, 3H). MS (ES$^+$): 251.1 (M+H)$^+$.

Preparation of 7-Chloro-2-methyl-8-(2,2,2-trichloro-ethyl)-quinoxaline

Tin(II)-chloride dihydrate (21.7 g, 96.12 mmol, 5.4 equiv) was added at room temperature to a solution of 7-chloro-2-methyl-8-nitro-quinoxaline (3.98 g, 17.80 mmol) in a mixture of EtOAc (56 ml) and ethanol (28 ml). After 40 minutes at 80° C., the reaction mixture was cooled to room temperature, diluted with ice water, filtered, and extracted with EtOAc. The combined organic layers were washed with concentrated aqueous NaHCO$_3$ solution and brine, dried over Na$_2$SO$_4$, filtered, and concentrated in vacuo to afford 6-chloro-3-methyl-quinoxalin-5-ylamine, which was used in the next transformation without purification. MS (ES$^+$): 194.2 (M+H)$^+$.

Tert-butylnitrite (2.74 g, 26.60 mmol, 1.5 equiv) was added to a suspension of copper(II) chloride (2.86 g, 21.28 mmol, 1.2 equiv) in anhydrous acetonitrile (25 ml). 1,1-Dichloroethene (25.8 g, 266 mmol, 15 equiv) and a solution of 6-chloro-3-methyl-quinoxalin-5-ylamine (3.43 g, 17.74 mmol) in anhydrous acetonitrile (16 ml) were added. After 4 hours at room temperature, concentrated aqueous NH$_4$Cl solution and EtOAc were added. The mixture was filtered and extracted with EtOAc. The combined organic layers were washed with brine, dried over Na$_2$SO$_4$, filtered and concentrated in vacuo. The residue was purified via flash chromatography (gradient of hexane/EtOAc 100:0 to 90:10) to afford the title compound (3.08 g, 56%) as an oil. $^1$H NMR (400 MHz, CDCl$_3$): δ=8.71 (s, 1H), 8.02 (d, J=8.8 Hz, 1H), 7.74 (d, J=8.8 Hz, 1H), 4.98 (s, 2H), 2.77 (s, 3H). MS (ES$^+$): 310 (M+H)$^+$.

Preparation of 7-Chloro-2-methyl-8-nitro-quinoxaline

At room temperature, 2-oxo-propionaldehyde (40% aqueous solution, 3.03 ml, 20.15 mmol, 1.0 equiv) was added to a solution of 4-chloro-3-nitro-benzene-1,2-diamine (3.78 g, 20.15 mmol) in THF (600 ml) and aqueous HCl (5N, 9.5 ml). The mixture was warmed to 65° C. for 10 minutes, then it was concentrated to approximately 200 ml and extracted with EtOAc. The combined organic layers were washed with dilute aqueous NaHCO$_3$ solution and brine, dried over Na$_2$SO$_4$, filtered and concentrated in vacuo. The residue was purified via flash chromatography (gradient of hexane/EtOAc 9:1 to 7:3) to afford the title compound (3.86 g, 81%, 92:8 mixture of 7-chloro-2-methyl-8-nitro-quinoxaline and 6-chloro-2-methyl-5-nitro-quinoxaline). $^1$H NMR (400 MHz, CDCl$_3$): δ=8.81 (s, 1H), 8.15 (d, J=9.1 Hz, 1H), 7.74 (d, J=9.1 Hz, 1H), 2.79 (s, 3H). MS (ES$^+$): 224 (M+H)$^+$.

Preparation of 4-Chloro-3-nitro-benzene-1,2-diamine

At room temperature, an aqueous solution of hydroiodic acid (48%, 25 ml) was added to a solution of 5-chloro-4-nitro-benzo[1,2,5]selenadiazole (8.14 g, 31.01 mmol) in concentrated aqueous hydrochloric acid (76 ml). After 2 hours at room temperature, a 5% aqueous solution of NaHSO$_3$ (150 ml) was added, and the mixture was stirred for 15 minutes. At 0° C., concentrated aqueous NaOH solution was added until the pH value reached 8. The mixture was extracted with EtOAc. The combined organic layers were dried over Na$_2$SO$_4$, filtered and concentrated in vacuo to afford the title compound (4.98 g, 86%), which was used in the next transformation without further purification. $^1$H NMR (400 MHz, d$_6$-acetone): δ=6.81 (d, J=7.7 Hz, 1H), 6.68 (d, J=7.7 Hz, 1H), 5.12 (br s, 2H), 4.78 (br s, 2H). MS (ES$^-$): 186.2 (M–H)$^-$.

Preparation of 5-Chloro-4-nitro-benzo[1,2,5]selenadiazole

At 0-5° C., a 65% aqueous solution of HNO$_3$ (6.5 g, 103.5 mmol, 3.3 equiv) was added to a solution of 5-chloro-benzo[1,2,5]selenadiazole (6.82 g, 31.35 mmol; $^1$H NMR (400 MHz, d$_6$-DMSO): δ=7.96 (d, J=1.4 Hz, 1H), 7.82 (d, J=10.2 Hz, 1H), 7.52 (dd, J=10.2/1.4 Hz, 1H)) in sulfuric acid (95-97%, 100 ml). After 2 hours at 5° C., the reaction mixture was poured onto ice water, and the precipitate was filtered off. The solid was washed with water and dried under high vacuum to afford the title compound (8.14 g, 99%). $^1$H NMR (400 MHz, d$_6$-DMSO): δ=8.13 (d, J=8.5 Hz, 1H), 7.82 (d, J=8.5 Hz, 1H).

EXAMPLES 166-168

By following the procedures of Example 165, but by using the appropriate starting materials, the compounds of formula G wherein R$_a$, R$_1$, R$_2$ and R$_3$, are as indicated in Table 7 below, and R$_c$, R$_d$, and R$_e$ is H, may be obtained.

TABLE 7

G (structure shown)

| | $R_1$ | $R_2$ | $R_a$ | MS |
|---|---|---|---|---|
| 166. | OH | —CH$_2$N(CH$_3$)$_2$ | H | MH$^+$ 414 |
| 167. | OH | —CH$_2$N(CH$_3$)$_2$ | CH$_3$ | MH$^+$ 428 |
| 168. | Cl | —CH$_2$N(CH$_3$)$_2$ | CH$_3$ | MH$^+$ 446 |

EXAMPLE 169

3-(3-Chloro-8-dimethylaminomethyl-naphthalen-2-yl)-4-(1-methyl-1H-indol-3-yl)-pyrrole-2,5-dione

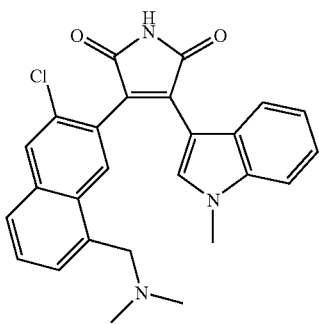

Potassium tert-butoxide (1.0 M in THF, 0.26 ml, 0.26 mmol, 3.0 equiv) was added at room temperature under an atmosphere of argon to a solution of (1-methyl-1H-indol-3-yl)-oxo-acetic acid methyl ester (24 mg, 0.11 mmol, 1.3 equiv) and of crude 2-(3-chloro-8-dimethylaminomethyl-naphthalen-2-yl)-acetamide (24 mg) in anhydrous tetrahydrofuran (2.5 ml, dried over molecular sieves). The reaction mixture was stirred for 1 hour at room temperature. It was then diluted with EtOAc and poured into a saturated aqueous NH$_4$Cl solution. After three extractions with EtOAc, the combined organic layers were dried over Na$_2$SO$_4$, filtered and concentrated in vacuo. Purification of the residue via preparative HPLC afforded the title compound (4.9 mg, 4% for two steps) as its trifluoroacetate salt. $^1$H NMR (400 MHz, d$_6$-DMSO): δ=11.20 (s, 1H), 8.56 (s, 1H), 8.15 (s, 1H), 8.02 (s, 1H), 8.01-7.92 (m, 1H), 7.80-7.70 (m, 1H), 7.62-7.57 (m, 1H), 7.42 (d, J=8.1 Hz, 1H), 7.00 (t, J=7.9 Hz, 1H), 6.45 (t, J=7.5 Hz, 1H), 6.23 (d, J=8.0 Hz, 1H), 4.85-4.65 (br d, 2H), 3.87 (s, 3H), 2,85 (br s, 3H), 2.76 (br s, 3H). MS (ES$^+$): 444 (M+H)$^+$.

Preparation of 2-(3-Chloro-8-dimethylaminomethyl-naphthalen-2-yl)-acetamide

Palladium(II)-chloride (4.3 mg, 0.024 mmol, 0.1 equiv) and acetamide (60 mg, 1.0 mmol, 4.2 equiv) were added to a solution of (3-chloro-8-dimethylaminomethyl-naphthalen-2-yl)-acetonitrile in THF (0.75 ml) and water (0.25 ml). After 18 hours at room temperature, the reaction mixture was adsorbed on silica gel, concentrated to dryness, and purified via two flash columns. Since purification on silica gel failed to remove unreacted acetamide, the resulting mixture was used directly in the next step. MS (ES$^+$): 277 (M+H)$^+$.

Preparation of (3-Chloro-8-dimethylaminomethyl-naphthalen-2-yl)-acetonitrile

Triethylamine (0.12 ml, 0.87 mmol, 2.0 equiv) was added to a solution of (3-chloro-8-dimethylaminomethyl-naphthalen-2-yl)-methanol (109 mg, 0.44 mmol) in CH$_2$Cl$_2$ (1.5 ml). At −25° C., a solution of methanesulfonyl chloride (0.05 ml, 0.66 mmol, 1.5 equiv) in CH$_2$Cl$_2$ (1.5 ml) was then added dropwise. After 15 minutes at 0° C., cold water (4° C., 10 ml) was added, and the mixture was extracted with CH$_2$Cl$_2$ (2×40 ml). The combined organic layers were dried over Na$_2$SO$_4$, filtered and concentrated. The crude mesylate was dissolved in N,N-dimethylformamide (2 ml) and treated at 0° C. with potassium cyanide (39 mg, 0.60 mmol, 1.0 equiv). The reaction mixture was stirred at room temperature for 2 hours, until TLC analysis indicated complete conversion. After dilution with water (50 ml), the mixture was extracted with CH$_2$Cl$_2$ (2×200 ml). The combined organic layers were dried over Na$_2$SO$_4$, filtered and concentrated in vacuo. Purification via flash chromatography (hexane/EtOAc 100:0 to 80:20) afforded the title compound (54 mg, 48%, mixture of 2 regioisomers). The regioisomers could be separated by preparative HPLC. Data for (3-chloro-8-dimethylaminomethyl-naphthalen-2-yl)-acetonitrile: $^1$H NMR (400 MHz, CDCl$_3$): δ=8.20 (s, 1H), 8.04 (s, 1H), 7.93 (d, J=8.4 Hz, 1H), 7.72 (d, J=6.6 Hz, 1H), 7.55 (dd, J=8.4/6.6 Hz, 1H), 4.59 (s, 2H), 3.96 (s, 2H), 2.78 (s, 6H). MS (ES$^+$): 259 (M+H)$^+$.

Preparation of (3-Chloro-8-dimethylaminomethyl-naphthalen-2-yl)-methanol

Diisobutylaluminium hydride (1 M in THF, 4.2 ml, 4.1 mmol, 9.0 equiv) was added to a solution of 3-chloro-8-dimethylaminomethyl-naphthalene-2-carboxylic acid ethyl ester (133 mg, 0.46 mmol) in 3.2 ml anhydrous THF at 0° C. After 15 minutes at 0° C., TLC analysis revealed complete conversion of starting material. Water (30 ml) was added, and the mixture was extracted with EtOAc (2×100 ml). The combined organic layers were washed with brine, dried over Na$_2$SO$_4$, filtered and concentrated in vacuo. Purification via flash chromatography (gradient of CH$_2$Cl$_2$/MeOH 97:3 to 90:10) afforded the title compound (109 mg, 96%, mixture of 2 regioisomers) as a colorless oil. Data for (3-chloro-8-dimethylaminomethyl-naphthalen-2-yl)-methanol: $^1$H NMR (400 MHz, CDCl$_3$): δ=8.36 (s, 1H), 7.85 (s, 1H), 7.74 (dd, J=7.1/1.9 Hz, 1H), 7.44-7.39 (m, 2H), 4.94 (s, 2H), 4.06 (s, 2H), 2.45 (s, 6H). MS (ES$^+$): 250 (M+H)$^+$.

Preparation of 3-Chloro-8-dimethylaminomethyl-naphthalene-2-carboxylic acid ethyl ester A solution of dimethylamine (5.6 M in EtOH, 0.36 ml, 2.0 mmol, 1.5 equiv) was added to a solution of 3-chloro-8-formyl-naphthalene-2-carboxylic acid ethyl ester (350 mg, 1.33 mmol) in THF (6.5 ml). After stirring at room temperature for 16 hours, a solution of sodium cyanoborohydride (101 mg, 1.6 mmol, 1.2 equiv) in MeOH (3.0 ml) and acetic acid (0.38 ml, 6.7 mmol, 5.0 equiv) were added, and the reaction mixture was stirred at room temperature for 3 hours.

After dilution with water (75 ml), the mixture was extracted with CH$_2$Cl$_2$ (total of 400 ml). The combined organic layers were washed with concentrated aqueous NaHCO$_3$ solution, dried over Na$_2$SO$_4$, filtered and concentrated in vacuo. The residue was purified via flash chromatography (gradient of hexane/EtOAc 100:0 to 1:2) to afford the title compound (133 mg, 34%) as a mixture of regioisomers, which could be separated for analytical purposes. 3-Chloro-8-dimethylaminomethyl-naphthalene-2-carboxylic acid ethyl ester: $^1$H NMR (400 MHz, CDCl$_3$): δ=8.72 (s, 1H), 8.08 (s, 1H), 7.87 (d, J=7.7 Hz, 1H), 7.61-7.55 (m, 2H), 4.42 (q, J=7.1 Hz, 2H), 3.97 (br s, 2H), 2.33 (s, 6H), 1.40 (t, J=7.1 Hz, 3H). MS (ES$^+$): 292 (M+H)$^+$. 3-Chloro-5-dimethylaminomethyl-naphthalene-2-carboxylic acid ethyl ester: $^1$H NMR (400 MHz, CDCl$_3$): δ=8.39 (s, 1H), 8.35 (s, 1H), 7.94 (d, J=7.8 Hz, 1H), 7,57-7.50 (m, 2H), 4.41 (q, J=7.1 Hz, 2H), 3.81 (s, 2H), 2.24 (s, 6H), 1.40 (t, J=7.1 Hz, 3H). MS (ES$^+$): 292 (M+H)$^+$.

Preparation of
3-Chloro-8-formyl-naphthalene-2-carboxylic acid ethyl ester

NaH$_2$PO$_2$ x H$_2$O (2.12 g, 20.02 mmol, 8.0 equiv) and Raney nickel (1.50 g) were added at room temperature to a solution of 3-chloro-8-cyano-naphthalene-2-carboxylic acid ethyl ester (0.65 g, 2.50 mmol) in pyridine (16 ml)/AcOH (8 ml)/H$_2$O (8 ml). The heterogeneous mixture was heated to 125° C. for 2 hours. After cooling and filtering off the Raney nickel catalyst, the reaction mixture was diluted with water (100 ml). After extraction with EtOAc (2×400 ml), the combined organic layers were washed with brine (2×50 ml), dried over Na$_2$SO$_4$, filtered and concentrated in vacuo. The residue was purified via flash chromatography (gradient of hexane/EtOAc 100:0 to 90:10) to afford the title compound (350 mg, 53%, inseparable 1:1.5 mixture of regioisomers A:B) as a white solid. $^1$H NMR (400 MHz, CDCl$_3$): δ=10.35 (s, 1H isomer B), 10.33 (s, 1H isomer A), 9.70 (s, 1H isomer B), 9.41 (s, 1H isomer A), 8.39 (s, 1H isomer A), 8.14 (d, J=8.4 Hz, 1H isomer A). 8.08 (dd, J=7.1/1.2 Hz, 1H isomer B), 8.04-8.01 (m, 1H isomer A+1H isomer B), 7.99 (1H isomer B), 7.77-7.70 (m, 1H isomer A+1H isomer B), 4.48 (q, J=7.1 Hz, 2H isomer B), 4.47 (q, J=7.1 Hz, 2H isomer A), 1.46 (t, J=7.1 Hz, 3H isomer B), 1.45 (t, J=7.1 Hz, 3H isomer A). MS (ES$^+$): 263 (M+H)$^+$.

Preparation of
3-Chloro-8-cyano-naphthalene-2-carboxylic acid ethyl ester

Zn(CN)$_2$ (1.50 g, 12.80 mmol, 2.0 equiv) and Pd(PPh$_3$)$_4$ (296 mg, 0.26 mmol, 0.04 equiv) were added at room temperature under an atmosphere of argon to a degassed solution of 3-chloro-8-trifluoromethanesulfonyloxy-naphthalene-2-carboxylic acid ethyl ester (2.45 g, 6.40 mmol) in N,N-dimethylformamide (25 ml). The mixture was heated to 125° C. After 30 minutes, TLC analysis indicated complete conversion. After cooling, water was added, and the mixture was extracted with EtOAc. The combined organic layers were washed with brine, dried over Na$_2$SO$_4$, filtered and concentrated in vacuo. Purification via flash chromatography (gradient of hexane/EtOAc 100:0 to 90:10) afforded the title compound (1.43 g, 86%, 1:1.3 mixture of regioisomers A:B) as a white solid. For analytical purposes, the regioisomers could be separated by careful chromatography on silica gel. Regioisomer A: $^1$H NMR (400 MHz, CDCl$_3$): δ=8.41 (s, 1H), 8.32 (s, 1H), 8.13 (br d, J=8.3 Hz, 1H), 8.01 (dd, J=7.1/1.0 Hz, 1H), 7.60 (dd, J=8.3/7.3 Hz, 1H), 4.47 (q, J=7.1 Hz, 2H), 1.45 (t, J=7.1 Hz, 3H). MS (ES$^+$): 260 (M+H)$^+$. Regioisomer B: $^1$H NMR (400 MHz, CDCl$_3$): δ=8.65 (s, 1H), 8.02 (d, J=8.3 Hz, 1H), 8.02 (s, 1H), 7.96 (dd, J=7.4/1.3 Hz, 1H), 7.65 (dd, J=8.3/7.4 Hz, 1H), 4.49 (q, J=7.1 Hz, 2H), 1.46 (t, J=7.3 Hz, 3H). MS (ES$^+$): 260 (M+H)$^+$.

Preparation of 3-Chloro-8-trifluoromethanesulfonyloxy-naphthalene-2-carboxylic acid ethyl ester Trifluoromethanesulfonic anhydride (2.46 g, 8.73 mmol, 1.2 equiv) was added at −20° C. under an atmosphere of argon to a solution of 3-chloro-8-hydroxy-naphthalene-2-carboxylic acid ethyl ester (1.82 g, 7.28 mmol) in pyridine (55 ml). After 1 hour at 0° C., an additional portion of trifluoromethanesulfonic anhydride (2.46 g, 8.73 mmol, 1.2 equiv) was added, and stirring was continued at 0° C. for another 1.5 hours. Cold water (4° C., 100 ml) was carefully added, and the reaction mixture was extracted with EtOAc (1 liter in total). The combined organic layers were washed with concentrated aqueous NH$_4$Cl solution and brine, dried over Na$_2$SO$_4$, filtered and concentrated in vacuo. Purification via flash chromatography (slow gradient of hexane/EtOAc 100:0 to 90:10) afforded the title compound (2.45 g, 88%, inseparable 1:1.3 mixture of regioisomers A:B) as an oil. $^1$H NMR (400 MHz, CDCl$_3$): δ=8.56 (s, 1H isomer B), 8.40 (s, 1H isomer A), 8.12 (s, 1H isomer A), 8.01 (s, 1H isomer B), 7.93-7.91 (m, 1H isomer A), 7.81 (d, J=8.6 Hz, 1H isomer B), 7.62-7.51 (m, 2H isomer A+2H isomer B), 4.47 (q, J=7.1 Hz, 2H isomer A+2H isomer B), 1.45 (t, J=7.1 Hz, 3H isomer A+3H isomer B). $^{19}$F NMR (377 MHz, CDCl$_3$): δ=−73.02. MS (ES$^+$): 383 (M+H)$^+$.

Preparation of
3-Chloro-8-hydroxy-naphthalene-2-carboxylic acid ethyl ester

Tetrabutylammonium iodide (3.74 g, 10.12 mmol, 1.3 equiv) was added to a solution of 3-chloro-8-methoxy-naphthalene-2-carboxylic acid ethyl ester (2.06 g, 7.79 mmol) in anhydrous CH$_2$Cl$_2$ (39 ml). After cooling to −78° C., BCl$_3$ (1M solution in CH$_2$Cl$_2$, 19.46 ml, 19.46 mmol, 2.5 equiv) was added dropwise. The reaction mixture was stirred at −78° C. for 30 minutes and then let warm to room temperature. After 2 hours at room temperature, cold water (4° C., 40 ml) was added slowly, and the resulting mixture was vigorously stirred for 30 minutes before it was extracted with EtOAc (800 ml total). The combined organic layers were washed with concentrated aqueous NaHCO$_3$ solution (100 ml) and concentrated aqueous NH$_4$Cl solution (100 ml), dried over Na$_2$SO$_4$, filtered and concentrated in vacuo. Purification via flash chromatography (gradient of hexane/EtOAc 100:0 to 6:4) afforded the title compound (1.84 g, 95%, inseparable 1:1.3 mixture of regioisomers A:B) as a slightly yellow solid. $^1$H NMR (400 MHz, d$_6$-DMSO): δ=10.69 (br s, 1H isomer B), 10.55 (br s, 1H isomer A), 8.60 (s, 1H isomer B), 8.35 (s, 1H isomer A), 8.16 (s, 1H isomer A), 8.06 (s, 1H isomer B), 7.55-7.36 (m, 2H isomer A+2H isomer B), 7.01 (d, J=7.6 Hz, 1H isomer A), 6.95 (d, J=7.5 Hz, 1H isomer B), 4.36 (q, J=7.1 Hz, 2H isomer A+2H isomer B), 1.37-1.33 (m, 3H isomer A+3H isomer B). MS (ES$^+$): 251 (M+H)$^+$.

Preparation of
3-Chloro-8-methoxy-naphthalene-2-carboxylic acid ethyl ester

A solution of NaNO$_2$ (884 mg, 12.81 mmol, 1.45 equiv) in water (20 ml) was added dropwise at 0° C. to a solution of 3-amino-8-methoxy-naphthalene-2-carboxylic acid ethyl ester (2.165 g, 8.83 mmol) in 18% aqueous HCl (50 ml). After it was stirred for 30 minutes at 0° C., this mixture was added dropwise at −20° C. to a solution of freshly prepared Cu(I)Cl (2.62 g, 26.50 mmol, 3.0 equiv) in concentrated aqueous HCl (90 ml). After 1 hour at −10° C. and 1 hour at rt, solid NaHCO$_3$ was carefully added to the reaction mixture until pH was >7.0. After dilution with water (200 ml), the aqueous phase was extracted with EtOAc (2 liters in total). The combined organic layers were washed with water (300 ml) and concentrated aqueous NH$_4$Cl solution (100 ml), dried over Na$_2$SO$_4$, filtered and concentrated in vacuo. Purification via flash chromatography (gradient of hexane/EtOAc 10:0 to 9:1) afforded the title compound (1.36 g, 58%, inseparable ~1:1 mixture of regioisomers A:B) as a slightly yellow oil. $^1$H NMR (400 MHz, CDCl$_3$): δ=8.76 (s, 1H isomer A/B), 8.31 (s, 1H isomer A/B), 7.85 (s, 1H isomer A/B), 7.50-7.40 (m, 3H isomer A/B), 7.32 (d, J=8.6 Hz, 1H isomer A/B), 6.90 (dd, J=6.6/2.0 Hz, 1H isomer A/B), 6.83 (d, J=7.6 Hz, 1H isomer A/B), 4.44 (q, J=7.1 Hz, 2H), 4.01 (s, 3H isomer A/B), 4.00 (s, 3H isomer A/B), 1.44 (t, J=7.1 Hz, 3H isomer A/B), 1.44 (t, J=7.1 Hz, 3H isomer A/B). MS (ES$^+$): 265 (M+H)$^+$.

Preparation of
3-Amino-8-methoxy-naphthalene-2-carboxylic acid ethyl ester

Palladium-on-carbon (10%, 1.281 g, 1.204 mol, 0.1 equiv) was added under an atmosphere of argon to a solution of 8-methoxy-3-nitro-naphthalene-2-carboxylic acid ethyl ester (3.313 g, 12.04 mmol) in EtOH (50 ml). The atmosphere was replaced by hydrogen gas, and the mixture was stirred at room temperature for 3 hours (hydrogen balloon). The atmosphere was changed back to argon, the catalyst was filtered off and the filtrate was concentrated in vacuo to afford the title compound (2.820 g, 96%, inseparable 1:1.15 mixture of regioisomers A:B) of adequate purity for direct use in the next transformation. $^1$H NMR (400 MHz, CDCl$_3$): δ=8.88 (s, 1H isomer B), 8.44 (s, 1H isomer A), 7.36 (s, 1H isomer A), 7.32-7.26 (m, 1H isomer A+1H isomer B), 6.91 (s, 1H isomer B), 6.73 (d, J=7.4 Hz, 1H isomer A), 6.50 (d, J=7.6 Hz, 1H isomer B), 4.41 (q, J=7.0 Hz, 2H isomer B), 4.40 (q, J=7.1 Hz, 2H isomer A), 3.97 (s, 3H isomer B), 3.96 (s, 3H isomer A), 1.44 (t, J=7.1 Hz, 3H isomer B), 1.44 (t, J=7.0 Hz, 3H isomer A). MS (ES$^+$): 246 (M+H)$^+$.

Preparation of
8-Methoxy-3-nitro-naphthalene-2-carboxylic acid ethyl ester

A solution of 3-nitro-propionic acid ethyl ester (16.25 g, 110.45 mmol, 4.0 equiv) in EtOH (150 ml) was added at 0° C. under an atmosphere of argon to a freshly prepared solution of sodium (2.54 g, 110.45 mmol, 4.0 equiv) in EtOH (110 ml). After 15 minutes, a solution of 3-methoxy-benzene-1,2-dicarbaldehyde (4.53 g, 27.61 mmol) in EtOH (150 ml) was added at 0° C. The reaction mixture was warmed to room temperature, and after 40 minutes, TLC analysis indicated complete conversion. 2 N aqueous HCl (55 ml, 4 equiv) was carefully added at 0° C., and the mixture was extracted with EtOAc (1.5 liter in total). The combined organic layers were washed with concentrated aqueous NH$_4$Cl solution (200 ml), brine (400 ml), dried over Na$_2$SO$_4$, filtered and concentrated in vacuo. The residue was purified via flash chromatography (gradient of toluene/hexane 5:5 to 10:0) to afford the title compound (0.942 g, 12%, inseparable 1:1.15 mixture of regioisomers A:B) as a yellow oil. $^1$H NMR (400 MHz, CDCl$_3$): δ=8.87 (s, 1H isomer A), 8.69 (s, 1H isomer B), 8.33 (s, 1H isomer B), 8.15 (s, 1H isomer A), 7.64-7.59 (m, 1H isomer A+1H isomer B), 7.53 (d, J=8.1 Hz, 1H isomer B), 7.51 (d, J=8.3 Hz, 1H isomer A), 7.02 (d, J=6.5 Hz, 1H isomer B), 7.00 (d, J=7.8 Hz, 1H isomer A), 4.42 (q, J=7.3 Hz, 2H isomer A), 4.41 (q, J=7.1 Hz, 2H isomer B), 4.04 (s, 3H isomer A), 4.03 (s, 3H isomer B), 1.38 (t, J=6.3 Hz, 3H isomer A+3H isomer B). MS (ES$^+$): 276 (M+H)$^+$.

Preparation of
3-Methoxy-benzene-1,2-dicarbaldehyde

A solution of DMSO (63.35 g, 810.8 mmol, 4.4 equiv) in CH$_2$Cl$_2$ (190 ml) was slowly added at −78° C. under an atmosphere of argon to a solution of oxalyl chloride (51.46 g, 405.4 mmol, 2.2 equiv) in CH$_2$Cl$_2$ (600 ml). A solution of (2-hydroxymethyl-6-methoxy-phenyl)-methanol (30.97 g, 184.3 mmol) in CH$_2$Cl$_2$ (250 ml) was added dropwise, while maintaining the temperature of the reaction mixture below −68° C. 90 minutes after completed addition, triethylamine (335.65 g, 3.317 mol, 18 equiv) was slowly added at −78° C. The reaction mixture was warmed to room temperature over 2 hours, at which point TLC analysis indicated complete conversion. Water (500 ml) was added, and the mixture was extracted with CH$_2$Cl$_2$ (4 liters in total). The combined organic layers were dried over Na$_2$SO$_4$, filtered and concentrated in vacuo. Purification of the residue via flash chromatography (gradient of hexane/EtOAc 100:0 to 0:100) afforded 28.78 g of a orange-brown solid, which was recrystallized from CH$_2$Cl$_2$/hexane to give a first crop of pure title compound (brown solid, 9.68 g). Further purification of the mother liquor via flash chromatography and recrystallization afforded another 7.95 g of pure title compound (total: 17.63 g, 58%). $^1$H NMR (400 MHz, CDCl$_3$): δ=10.64 (s, 1H), 10.42 (s, 1H), 7.64 (t, J=7.9 Hz, 1H), 7.44 (d, J=7.8 Hz, 1H), 7.23 (dd, J=8.5/0.9 Hz, 1H), 3.97 (s, 3H). MS (ES$^+$): 165 (M+H)$^+$.

Preparation of
(2-Hydroxymethyl-6-methoxy-phenyl)-methanol

A solution of 7-methoxy-3H-isobenzofuran-1-one (16.65 g, 101.4 mmol) in anhydrous THF (200 ml) was added at room temperature under an atmosphere of argon to a freshly prepared solution of LiAlH$_4$ (7.70 g, 202.8 mmol, 2.0 equiv) in THF (100 ml). After 30 minutes at room temperature, TLC analysis indicated complete conversion. The reaction mixture was cooled to 0° C. and water was added dropwise until gas evolution ceased. Water (500 ml) and CH$_2$Cl$_2$ (500 ml) was added to form a white suspension. After filtration, the filtrate was extracted with CH$_2$Cl$_2$ (4 liters in total). The combined organic layers were dried over Na$_2$SO$_4$, filtered and concentrated in vacuo to afford the title compound (15.34 g, 90%) in adequate purity for direct use in the next transformation. $^1$H NMR (400 MHz, CDCl$_3$): δ=7.27 (t, J=7.8 Hz, 1H), 6.96 (d, J=7.3 Hz, 1H), 6.89 (d, J=8.3 Hz, 1H), 4.83 (s, 2H); 4.72 (s, 2H), 3.85 (s, 3H), 2.8-2.6 (br s, 2H). MS (ES$^+$): 169 (M+H)$^+$.

Preparation of 7-Methoxy-3H-isobenzofuran-1-one

Solid sodium borohydride (14.02 g, 370.5 mmol, 1.75 equiv) was added in portions to a solution of N,N-diethyl-2- formyl-6-methoxy-benzamide (49.81 g, 211.7 mmol) in methanol (800 ml) at 0° C. After complete addition, stirring was continued at room temperature for 30 minutes, until TLC analysis indicated complete consumption of starting material. The reaction mixture was cooled to 0° C., and 6N aqueous HCl (134 ml) was carefully added. The solution was heated to 90° C. for 90 minutes. After cooling, volatiles were removed in vacuo. The residue was taken up in water (500 ml) and extracted four times with EtOAc (1.6 liter in total). The combined organic layers were washed with brine (2×100 ml), dried over $Na_2SO_4$, filtered and concentrated in vacuo to afford the title compound (33.92 g, 98%) in adequate purity for direct use in the next transformation. $^1$H NMR (400 MHz, $CDCl_3$): δ=7.60 (t, J=8.4 Hz, 1H), 7.00 (d, J=7.6 Hz, 1H), 6.91 (d, J=8.3 Hz, 1H), 5.22 (s, 2H), 3.98 (s, 3H). MS ($ES^+$): 165 $(M+H)^+$.

Preparation of N,N-Diethyl-2-formyl-6-methoxy-benzamide

Sec-butyl lithium (99.6 ml, 1.3 M in cyclohexane, 129.45 mmol, 1.3 equiv) was added dropwise at −78° C. to a solution of N,N,N',N'-tetramethyl-ethane-1,2-diamine (15.04 g, 129.45 mmol, 1.3 equiv) in anhydrous THF (400 ml) under an atmosphere of argon. After 30 minutes at −78° C., a solution of N,N-diethyl-2-methoxy-benzamide (20.64 g, 99.58 mmol) in THF (100 ml) was added dropwise over 50 minutes. After 2 hours at −78° C., N,N-dimethylformamide (8.74 g, 119.49 mmol, 1.2 equiv) was added dropwise. 30 minutes after complete addition, TLC analysis indicated complete conversion. 6N aqueous HCl (90 ml) was carefully added at 0° C. After phase separation, the aqueous phase was extracted with EtOAc. The combined organic layers were washed with brine (2×100 ml), dried over $Na_2SO_4$, filtered and concentrated in vacuo to yield the title compound (24.71 g, quant.) in adequate purity for direct use in the next transformation. $^1$H NMR (400 MHz, $CDCl_3$): δ=9.99 (s, 1H), 7.52 (dd, J=6.6/1.0 Hz, 1H), 7.46 (t, 7.6 Hz, 1H), 7.15 (dd, J=8.3/1.2 Hz, 1H), 3.86 (s, 3H), 3.78-3.68 (m, 1H), 3.58-3.49 (m, 1H), 3.10 (q, J=7.1 Hz, 2H), 1.29 (t, J=7.1 Hz, 3H), 1.01 (t, J=7.3 Hz, 3H). MS ($ES^+$): 236 $(M+H)^+$.

Preparation of N,N-Diethyl-2-methoxy-benzamide

N,N-dimethylformamide (0.52 ml, 6.70 mmol, 0.034 equiv) was added dropwise to a solution of 2-methoxy-benzoic acid (30.0 g, 197.2 mmol) in thionyl chloride (200 ml) at room temperature under an atmosphere of argon. The solution was stirred at room temperature for 45 minutes. Volatiles were removed in vacuo, and the residue was azeotroped with toluene (2×100 ml). The acid chloride was dissolved in anhydrous THF (220 ml), cooled to 0° C., and diethylamine (105 ml, 1.01 mol, 5.1 equiv) was added dropwise. The suspension was stirred at 0° C. for 10 minutes, when TLC analysis indicated complete conversion. The reaction mixture was diluted with water (50 ml) and extracted three times with EtOAc. The combined organic layers were washed with water (100 ml) and concentrated aqueous $NH_4Cl$ solution (50 ml), dried over $Na_2SO_4$, filtered and concentrated in vacuo. Purification of the residue via flash chromatography (gradient of hexane/EtOAc 6:4 to 3:7) afforded the title compound (40.87 g, quant.). $^1$H NMR (400 MHz, $CDCl_3$): δ=7.31 (ddd, J=9.0/7.3/1.7 Hz, 1H), 7.17 (dd, J=7.1 Hz/1.5 Hz, 1H), 6.95 (dt, J=7.5/1.0 Hz, 1H), 6.89 (br d, J=8.3 Hz, 1H), 3.80 (s, 3H), 3,62-3.48 (br m, 2H), 3.13 (q, J=7.4 Hz, 2H), 1.23 (t, J=7.1 Hz, 3H), 1.02 (t, J=7.1 Hz, 3H). MS ($ES^+$): 208 $(M+H)^+$.

EXAMPLES 170-177

By following the procedures of Example 169, but by using the appropriate starting materials, the compounds of formula H wherein $R_a$, $R_b$, $R_1$, $R_2$, $R_3$ and $R_4$ are as indicated in Table 8 below, and $R_c$, $R_d$, and $R_e$ is H, may be obtained.

TABLE 8

H

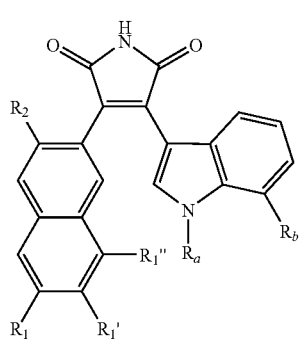

| | $R_2$ | $R_1$ | $R_{1'}$ | $R_{1''}$ | $R_a$ | $R_b$ | MS |
|---|---|---|---|---|---|---|---|
| 170. | H | —$CH_2NH_2$ | H | H | $CH_3$ | H | $MH^+$ 382 |
| 171. | H | H | H | —$CH_2NH_2$ | $CH_3$ | H | $MH^+$ 382 |
| 172. | Cl | —$CH_2N(CH_3)_2$ | H | H | H | H | $MH^+$ 430 |
| 173. | Cl | H | —$CH_2N(CH_3)_2$ | H | H | H | $MH^+$ 430 |
| 174. | Cl | — | —$CH_2N(CH_3)_2$ | H | H | $CH_3$ | $MH^+$ 444 |
| 175. | Cl | —$CH_2N(CH_3)_2$ | H | H | H | $CH_3$ | $MH^+$ 444 |
| 176. | Cl | H | —$CH_2N(CH_3)_2$ | H | $CH_3$ | H | $MH^+$ 444 |
| 177. | Cl | —$CH_2N(CH_3)_2$ | H | H | $CH_3$ | H | $MH^+$ 444 |

EXAMPLE 178

By following the procedures of Example 1, but by using the appropriate starting materials, the compound of formula D may be obtained. MH⁺ 487.

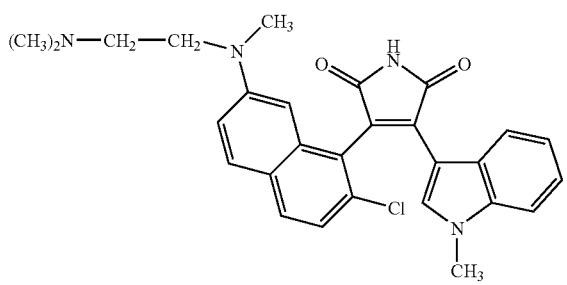

The compounds of the invention, i.e. of formulae (I), (II), (IIa), (IIb), (IIc) and (III), in free form or in pharmaceutically acceptable salt form, exhibit valuable pharmacological properties, e.g. inhibiting Protein Kinase C (PKC), e.g. PKC isoforms like α, β, δ, ε, η or θ activity, in particular the isoforms α and β, inhibiting T-cell activation and proliferation, e.g. by inhibiting production by T-cells or cytokines, e.g. IL-2, by inhibiting the proliferative response of T-cells to cytokines, e.g. IL-2, e.g. as indicated in vitro and in vivo tests and are therefore indicated for therapy.

A. In vitro

1. Protein Kinase C Assay

The compounds of the invention are tested for their activity on different PKC isoforms according to the following method. Assay is performed in a white with clear bottom 384-well microtiterplate with non-binding surface. The reaction mixture (25 µl) contains 1.5 µM of a tridecapeptide acceptor substrate that mimics the pseudo substrate sequence of PKC a with the Ala→Ser replacement, 10 µM ³³P-ATP, 10 mM Mg(NO₃)₂, 0.2 mM CaCl₂, PKC at a protein concentration varying from 25 to 400 ng/ml (depending on the isotype used), lipid vesicles (containing 30 mol % phosphatidylserine, 5 mol % DAG and 65 mol % phosphatidylcholine) at a final lipid concentration of 0.5 mM, in 20 mM Tris-HCl buffer pH 7.4+0.1% BSA. Incubation is performed for 60 min at room temperature. Reaction is stopped by adding 50111 of stop mix (100 mM EDTA, 200 µM ATP, 0.1% Triton X-100, 0.375 mg/well streptavidin-coated SPA beads in phosphate buffered saline w/o Ca, Mg. After 10 min incubation at room temperature, the suspension is spun down for 10 min at 300 g. Incorporated radioactivity is measured in a Trilux counter for 1 min. $IC_{50}$ measurement is performed on a routine basis by incubating a serial dilution of inhibitor at concentrations ranging between 1-1000 µM. $IC_{50}$ values are calculated from the graph by curve fitting with XL Fit® software.

2. Protein Kinase C θ Assay

Human recombinant PKCθ is used under the assay conditions as described above. In this assay, compounds of the invention inhibit PKC θ with an $IC_{50} \leq 1$ µM.

3. Protein Kinase Cα Assay

Human recombinant PKCα was obtained from Oxford Biomedical Research and is used under the assay conditions as described under Section A.1 above. In this assay, compounds of the invention inhibit PKCα with an $IC_{50} \leq 1$ µM. For example, compound of example 20 inhibits PKCα with an $IC_{50}$ of 28 nM; compound of example 37 with an $IC_{50}$ of 3 nM, compound of example 38 with an $IC_{50}$ of 9 nM.

4. Protein Kinase Cβ1 Assay

Human recombinant PKCβ1 was obtained from Oxford Biomedical Research and is used under the assay conditions as described under Section A.1 above. In this assay, compounds of the invention inhibit PKCβ1 with an $IC_{50} \leq 1$ µM. For example, compound of example 20 inhibits PKCα with an $IC_{50}$ of 12.4 nM; compound of example 136 with an $IC_{50}$ of 51 nM; compound of example 146 with an $IC_{50}$ of 25 nM; compound of example 163 with an $IC_{50}$ of 41 nM.

5. Protein Kinase Cδ Assay

Human recombinant PKCδ was obtained from Oxford Biomedical Research and is used under the assay conditions as described under Section A.1 above. In this assay, compounds of the invention inhibit PKCδ with an $IC_{50 \leq 1}$ µM.

6. Protein Kinase Cε Assay

Human recombinant PKCε was obtained from Oxford Biomedical Research and is used under the assay conditions as described under Section A.1 above. In this assay, compounds of formula (I), (II) and (III) inhibit PKCε with an $IC_{50 \leq 1}$ µM.

7. Protein Kinase Cη Assay

Human recombinant PKCη was obtained from PanVera and is used under the assay conditions as described under Section A.1 above. In this assay, compounds of the invention inhibit PKCη with an $IC_{50} \leq 1$ µM.

8. CD28 Costimulation Assay

The assay is performed with Jurkat cells transfected with a human interleukin-2 promoter/reporter gene construct as described by Baumann G et al. in Transplant. Proc. 1992; 24:43-8, the β-galactosidase reporter gene being replaced by the luciferase gene (de Wet J., et al., Mol. Cell. Biol. 1987, 7(2), 725-737). Cells are stimulated by solid phase-coupled antibodies or phorbol myristate acetate (PMA) and the Ca⁺⁺ ionophore ionomycin as follows. For antibody-mediated stimulation Microlite TM1 microtiter plates (Dynatech) are coated with 3 µg/ml goat anti-mouse IgG Fc antibodies (Jackson) in 55 µl phosphate-buffered saline (PBS) per well for three hours at RT. Plates are blocked after removing the antibodies by incubation with 2% bovine serum albumin (BSA) in PBS (300 µl per well) for 2 hours at RT. After washing three times with 300 µl PBS per well, 10 ng/ml anti-T cell receptor antibodies (WT31, Becton & Dickinson) and 300 ng/ml anti-CD28 antibodies (15E8) in 50 µl 2% BSA/PBS are added as stimulating antibodies and incubated overnight at 4° C. Finally the plates are washed three times with 300 µl PBS per well. Seven three-fold serial dilutions of test compounds in duplicates in assay medium (RPMI 1640/10% fetal calf serum (FCS) containing 50 µM 2-mercaptoethanol, 100 units/ml penicillin and 100 µg/ml streptomycin) are prepared in separate plates, mixed with transfected Jurkat cells (clone K22 290_H23) and incubated for 30 minutes at 37° C. in 5% CO₂. 100 µl of this mixture containing 1×10⁵ cells are then transferred to the antibody-coated assay plates. In parallel 100 µl are incubated with 40 ng/ml PMA and 2 µM ionomycin. After incubation for 5.5 hours at 37° C. in 5% CO₂, the level of luciferase is determined by bioluminescence measurement. The plates are centrifuged for 10 min at 500 g and the supernatant is removed by flicking. Lysis buffer containing 25 mM Tris-phosphate, pH 7.8, 2 mM DTT, 2 mM 1.2-diaminocyclohexane-N,N,N',N-tetraacetic acid, 10% (v/v) glycerol and 1% (v/v) Triton X-100 is added (20 µl per well). The plates are incubated at RT for 10 minutes under constant shaking. Luciferase activity is assessed with a bioluminescence reader (Labsystem, Helsinki, Finland) after automatic addition of 50 μl per well luciferase reaction buffer containing 20 mM Tricine, 1.07 mM $(MgCO_3)_4$ $Mg(OH)_2 \times 5H_2O$, 2.67 mM $MgSO_4$, 0.1 mM EDTA, 33.3 mM DTT, 270 μM coenzyme A, 470 μM luciferin (Chemie Brunschwig AG), 530 μM ATP, pH 7.8. Lag time is 0.5 seconds, total measuring time is 1 or 2 seconds. Low control values are light units from anti-T cell receptor- or PMA-stimulated cells, high controls are from anti-T cell receptor/anti-CD28- or PMA/ionomycin-stimulated cells without any test sample. Low controls are subtracted from all values. The inhibition obtained in the presence of a test compound is calculated as percent inhibition of the high control. The concentration of test compounds resulting in 50% inhibition ($IC_{50}$) is determined from the dose-response curves. In this assay, compounds of the invention inhibit anti-T cell receptor/anti-CD28 and PMA/ionomycin stimulated Jurkat cells with an $IC_{50} \leq 1$ μM.

9. Allogeneic Mixed Lymphocyte Reaction (MLR)

The two-way MLR is performed according to standard procedures (J. Immunol. Methods, 1973, 2, 279 and Meo T. et al., Immunological Methods, New York, Academic Press, 1979, 227-39). Briefly, spleen cells from CBA and BALB/c mice ($1.6 \times 10^5$ cells from each strain per well in flat bottom tissue culture microtiter plates, $3.2 \times 10^5$ in total) are incubated in RPMI medium containing 10% FCS, 100 U/ml penicillin, 100 μg/ml streptomycin (Gibco BRL, Basel, Switzerland), 50 μM 2-mercaptoethanol (Fluka, Buchs, Switzerland) and serially diluted compounds. Seven three-fold dilution steps in duplicates per test compound are performed. After four days of incubation 1 μCi $^3$H-thymidine is added. Cells are harvested after an additional five-hour incubation period, and incorporated $^3$H-thymidine is determined according to standard procedures. Background values (low control) of the MLR are the proliferation of BALB/c cells alone. Low controls are subtracted from all values. High controls without any sample are taken as 100% proliferation. Percent inhibition by the samples is calculated, and the concentrations required for 50% inhibition ($IC_{50}$ values) are determined.

Results

The assays used are described herein above.

The ratios of the $IC_{50}$ value for PKC β to the $IC_{50}$ value for PKCα, of the $IC_{50}$ value for PKC δ to the $IC_{50}$ value for PKCα, of the $IC_{50}$ value for PKC δ to the $IC_{50}$ value for PKCα, of the $IC_{50}$ value for PKC ε to the $IC_{50}$ value for PKCα, of the $IC_{50}$ value for PKC η to the $IC_{50}$ value for PKCα, of the $IC_{50}$ value for PKC θ to the $IC_{50}$ value for PKCα, of the $IC_{50}$ value as determined by the MLR assay and to the $IC_{50}$ value as determined by the BM assay, obtained for some compounds of the invention are indicated in table 11.

PKC α, β, δ, ε, η and θ assays, MLR and BM assays, are as described hereinabove.

TABLE 11

| Example | β/α | δ/α | ε/α | η/α | θ/α | BM/MLR |
|---|---|---|---|---|---|---|
| (1) | 0.5 | 7.1 | 19.4 | 39.3 | 2.9 | 41.3 |
| (7) | 0.4 | 28.0 | >28.3 | >28.3 | 13.6 | 12.2 |
| (18) | 0.3 | 5.8 | 6.6 | 22.4 | 2.0 | 6.0 |
| (20) | 0.4 | 30.6 | >35.7 | >35.7 | 14.2 | >10 |
| (23) | 1.4 | 67.8 | >88.5 | >88.5 | 26.1 | 17.6 |
| (31) | 2.1 | 90.6 | 133.2 | >145 | 25.4 | >63.3 |

The compounds of the invention preferably show a selectivity of at least 10 fold, more preferably 20 fold, most preferably 100 fold for the PKCs α and β, and optionally θ, over one or more of the other PKC isoforms, e.g. over one or more PKC isoforms selected from δ, ε, η and θ, preferably over the PKC isoform δ, more preferably over the PKC isoforms ε and η, and even more preferably over the PKC isoforms δ, ε and η.

Selectivity for the α, β or θ isoforms of the PKC over one or more of the other PKC isoforms can be measured by comparing the $IC_{50}$ of the compound for the α, β or θ PKC to the $IC_{50}$ of the compound for the other PKC isoforms, e.g. δ, ε, η. Preferably, the selectivity can be determined by calculating the ratio of $IC_{50}$ of the compound for the δ, ε or η PKC isoforms to the $IC_{50}$ of the compound for the α, β or θ PKC. $IC_{50}$ values may be obtained, for example, according to the PKC assay described below.

The preferred compounds of the invention show an $IC_{50}$ value for the α and β, and optionally θ, PKCs of $\leq 1$ μM, preferably $\leq 10$ nM in the hereinabove mentioned assay.

B. In vivo

Rat Heart Transplantation

The strain combination used: Male Lewis ($RT^1$ haplotype) and BN ($RT^1$ haplotype). The animals are anaesthetised using inhalational isofluorane. Following heparinisation of the donor rat through the abdominal inferior vena cava with simultaneous exsanguination via the aorta, the chest is opened and the heart rapidly cooled. The aorta is ligated and divided distal to the first branch and the brachiocephalic trunk is divided at the first bifurcation. The left pulmonary artery is ligated and divided and the right side divided but left open. All other vessels are dissected free, ligated and divided and the donor heart is removed into iced saline.

The recipient is prepared by dissection and cross-clamping of the infra-renal abdominal aorta and vena cava. The graft is implanted with end-to-side anastomoses, using 10/0 monofilament suture, between the donor brachiocephalic trunk and the recipient aorta and the donor right pulmonary artery to the recipient vena cava. The clamps are removed, the graft tethered retroabdominally, the abdominal contents washed with warm saline and the animal is closed and allowed to recover under a heating lamp. Graft survival is monitored by daily palpation of the beating donor heart through the abdominal wall. Rejection is considered to be complete when heart beat stops. Increases of graft survival are obtained in animals treated with a compound of the invention administered orally at a daily dose of 1 to 30 mg/kg bid.

Graft v. Host Model

Spleen cells ($2 \times 10^7$) from Wistar/F rats are injected subcutaneously into the right hind footpad of (Wistar/F×Fischer 344)$F_1$ hybrid rats. The left footpad is left untreated. The animals are treated with the test compounds on 4 consecutive days (0-3). The popliteal lymph nodes are removed on day 7, and the weight differences between two corresponding lymph nodes are determined. The results are expressed as the inhibition of lymph node enlargement (given in percent) comparing the lymph node weight differences in the experimental groups to the weight difference between the corresponding lymph nodes from a group of animals left untreated with a test compound.

The compounds of the invention are, therefore, useful in the treatment and/or prevention of diseases or disorders mediated by T lymphocytes and/or PKC, e.g. acute or chronic rejection of organ or tissue allo- or xenografts, graft versus host diseases, atherosclerosis, vascular occlusion due to vascular injury such as angioplasty, restenosis, obesity, syndrome X, impaired glucose tolerance, polycystic ovary syndrome, hypertension, heart failure, chronic obstructive pulmonary disease, CNS diseases such as Alzheimer disease or amyotrophic lateral sclerosis, cancer, infectious diseases such as AIDS, septic shock or adult respiratory distress syndrome, ischemia/reperfusion injury e.g. myocardial infarction, stroke, gut ischemia, renal failure or hemorrhage shock, or traumatic shock, e.g. traumatic brain injury. The compounds of the invention are also useful in the treatment and/or prevention of T-cell mediated acute or chronic inflammatory diseases or disorders or autoimmune diseases e.g. rheumatoid arthritis, osteoarthritis, systemic lupus erythematosus, Hashimoto's thyroidis, multiple sclerosis, myasthenia gravis, diabetes type I or II and the disorders associated therewith, respiratory diseases such as asthma or inflammatory lung injury, inflammatory liver injury, inflammatory glomerular injury, cutaneous manifestations of immunologically-mediated disorders or illnesses, inflammatory and hyperproliferative skin diseases (such as psoriasis, atopic dermatitis, allergic contact dermatitis, irritant contact dermatitis and further eczematous dermatitises, seborrhoeic dermatitis), inflammatory eye diseases, e.g. Sjoegren's syndrome, keratoconjunctivitis or uveitis, inflammatory bowel disease, Crohn's disease or ulcerative colitis. For the above uses the required dosage will of course vary depending on the mode of administration, the particular condition to be treated and the effect desired. In general, satisfactory results are indicated to be obtained systemically at daily dosages of from about 0.1 to about 100 mg/kg body weight. An indicated daily dosage in the larger mammal, e.g. humans, is in the range from about 0.5 mg to about 2000 mg, conveniently administered, for example, in divided doses up to four times a day or in retard form.

The compounds of the invention are also useful in the treatment and/or prevention of cardiovascular diseases and disorders, e.g. hypertension, cardiovascular ischemia, or for improving cardiac function following ischemia.

The compounds of the invention are also useful in the treatment and/or prevention of ocular diseases and disorders, e.g. involving inflammation and neovascularization.

The compounds of the invention may be administered by any conventional route, in particular enterally, e.g. orally, e.g. in the form of tablets or capsules, or parenterally, e.g. in the form of injectable solutions or suspensions, topically, e.g. in the form of lotions, gels, ointments or creams, or in a nasal or a suppository form. Pharmaceutical compositions comprising a compound of the invention in free form or in pharmaceutically acceptable salt form in association with at least one pharmaceutical acceptable carrier or diluent may be manufactured in conventional manner by mixing with a pharmaceutically acceptable carrier or diluent. Unit dosage forms for oral administration contain, for example, from about 0.1 mg to about 500 mg of active substance.

Topical administration is e.g. to the skin. A further form of topical administration is to the eye.

The compounds of the invention may be administered in free form or in pharmaceutically acceptable salt form e.g. as indicated above. Such salts may be prepared in conventional manner and exhibit the same order of activity as the free compounds.

In accordance with the foregoing the present invention further provides:

1.1 A method for preventing or treating disorders or diseases mediated by T lymphocytes and/or PKC, e.g. such as indicated above, in a subject in need of such treatment, which method comprises administering to said subject an effective amount of a compound of the invention, e.g. a selective inhibitor of PKCs α and β, and optionally θ, or a pharmaceutically acceptable salt thereof;

1.2 A method for preventing or treating acute or chronic transplant rejection or T-cell mediated inflammatory or autoimmune diseases, e.g. as indicated above, in a subject in need of such treatment, which method comprises administering to said subject an effective amount of a compound of the invention, e.g. a selective inhibitor of PKCs α and β, and optionally θ, or a pharmaceutically acceptable salt thereof;

1.3 A method for preventing or treating cardiovascular diseases and disorders, e.g. hypertension, cardiovascular ischemia, or for improving cardiac function following ischemia; in a subject in need of such treatment, which method comprises administering to said subject an effective amount of a compound of the invention, e.g. a selective inhibitor of PKCs α and β, and optionally θ, or a pharmaceutically acceptable salt thereof;

1.4 A method for preventing or treating ocular diseases and disorders, e.g. involving inflammation and neovascularization, e.g. as indicated above, in a subject in need of such treatment, which method comprises administering to said subject an effective amount of a compound of the invention, e.g. a selective inhibitor of PKCs α and β, and optionally θ, or a pharmaceutically acceptable salt thereof;

2. A compound of the invention, e.g. a selective inhibitor of PKCs α and β, and optionally θ, in free form or in a pharmaceutically acceptable salt form for use as a pharmaceutical, e.g. in any of the methods as indicated under 1.1 to 1.4 above.

3. A pharmaceutical composition, e.g. for use in any of the methods as in 1.1 to 1.4 above comprising a compound of the invention, e.g. a selective inhibitor of PKCs α and β, and optionally θ, in free form or pharmaceutically acceptable salt form in association with a pharmaceutically acceptable diluent or carrier therefor.

4. A compound of the invention, e.g. a selective inhibitor of PKCs α and β, and optionally θ, or a pharmaceutically acceptable salt thereof for use in the preparation of a pharmaceutical composition for use in any of the method as in 1.1 to 1.4 above.

Compounds of the invention may be administered as the sole active ingredient or together with other drugs in immunomodulating regimens or other anti-inflammatory agents e.g. for the treatment or prevention of allo- or xenograft acute or chronic rejection or inflammatory or autoimmune disorders. For example, they may be used in combination with cyclosporines, or ascomycines or their immunosuppressive analogs or derivatives, e.g. cyclosporin A, ISA Tx247, FK-506, ABT-281, ASM 981; an mTOR inhibitor, e.g. rapamycin, 40-O-(2-hydroxyethyl)-rapamycin, CC1779, ABT578, or a rapalog, e.g. AP23573, AP23464, AP23675, AP23841, TAFA-93, biolimus 7 or biolimus 9 etc.; corticosteroids; cyclophosphamide; azathioprene; methotrexate; an EDG receptor agonist having accelerating lymphocyte homing properties, e.g. FTY 720 or an analogue thereof; leflunomide or analogs thereof; mizoribine; mycophenolic acid or a salt thereof, e.g. sodium salt; mycophenolate mofetil; 15-deoxyspergualine or analogs thereof; immunosuppressive monoclonal antibodies, e.g., monoclonal antibodies to leukocyte receptors, e.g., MHC, CD2, CD3, CD4, CD 11a/CD18, CD7, CD25, CD 27, B7, CD40, CD45, CD58, CD 137, ICOS, CD150 (SLAM), OX40, 4-1BB or their ligands, e.g. CD154; or other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y, or other adhesion molecule inhibitors, e.g. mAbs or low molecular weight inhibitors including LFA-1 antagonists, Selectin antagonists and VLA-4 antagonists. Compounds of the invention may also be administered together with an antiproliferative drug, e.g. a chemotherapeutic drug, e.g. as used in cancer treatment, including but not limited to aromatase inhibitors, antiestrogens, topoisomerase I inhibitors, topoisomerase II inhibitors, microtubule active agents, alkylating agents, histone deacetylase inhibitors, farnesyl transferase inhibitors, COX-2 inhibitors, MMP inhibitors, mTOR inhibitors, antineoplastic antimetabolites, platin compounds, compounds decreasing the protein kinase activity and further anti-angiogenic compounds, gonadorelin agonists, anti-androgens, bengamides, bisphosphonates, antiproliferative antibodies and temozolomide, or with an anti-diabetic drug, an insulin secretagogue or insulin secretion enhancer, e.g. a sulphonyl urea, e.g. tolbutamide, chlorpropamide, tolazamide, acetohexamide, 4-chloro-N-[(1-pyrrolidinylamino)carbonyl]-benzensulfonamide (glycopyramide), glibenclamide (glyburide), gliclazide, 1-butyl-3-metanilylurea, carbutamide, glibonuride, glipizide, gliquidone, glisoxepid, glybuthiazole, glibuzole, glyhexamide, glymidine, glypinamide, phenbutamide or tolylcyclamide, an oral insulinotropic agent derivative, e.g. a short acting insulin enhancer, e.g. meglitinide, repaglinide, a phenyl acetic acid derivative, e.g. nateglinide, a DPP IV inhibitor, e.g. 1-{2-[(5-cyanopyridin-2-yl)amino]ethylamino}acetyl-(2S)-cyano-pyrrolidine dihydrochloride, LAF237, GLP-1 or a GLP-1 agonist analog, or an insulin sensitizer e.g. a peroxisome proliferator activated receptor γ agonist (PPARγ), e.g. a glitazone, a non-glitazone type such as a N-(2-benzoylphenyl)-L-tyrosine analogue, e.g. GI-262570, or an oxolidinedione, e.g. JTT501, a dual PPARγ/PPARα agonist, e.g. DRF-554158, NC-2100 or N,N-622, a retinoid X receptor agonist or a rexinoid, e.g. 2-[1-(3,5,5,8,8-pentamethyl-5,6,7,8-tetrahydro-2-naphthyl)-cyclopropyl]-pyridine-5-carboxylic acid, 4-[(3,5,5,8,8-pentamethyl-5,6,7,8-tetrahydro-2-naphthyl)-2-carbonyl]-benzoic acid, 9-cis retinoic acid or an analog, derivative or a pharmaceutically acceptable salt thereof, in diabetes therapy, In accordance with the foregoing the present invention provides in a yet further aspect:

5. A method as defined above comprising co-administration, e.g. concomitantly or in sequence, of a therapeutically effective amount of an inhibitor of PKC or of T-cell activation and proliferation, e.g. a compound of the invention in free form or in pharmaceutically acceptable salt form, and a second drug substance, said second drug substance being an immunosuppressant, immunomodulatory, anti-inflammatory, antiproliferative or anti-diabetic drug, e.g. as indicated above.

6. A therapeutic combination, e.g. a kit, comprising a) an inhibitor of PKC or of T-cell activation and proliferation, e.g. a compound of the invention, in free form or in pharmaceutically acceptable salt form, and b) at least one second agent selected from an immunosuppressant, immunomodulatory, anti-inflammatory, antiproliferative and anti-diabetic drug. Component a) and component b) may be used concomitantly or in sequence. The kit may comprise instructions for its administration.

Where an inhibitor of PKC or of T-cell activation and proliferation, e.g. a compound of the invention, e.g. a selective inhibitor of PKCs α and β, and optionally θ, is administered in conjunction with other immunosuppressive/immunomodulatory, anti-inflammatory, antiproliferative or anti-diabetic therapy, e.g. for preventing or treating acute or chronic graft rejection or inflammatory or autoimmune disorders as hereinabove specified, dosages of the co-administered immunosuppressant, immunomodulatory, anti-inflammatory, antiproliferative or anti-diabetic compound will of course vary depending on the type of co-drug employed, e.g. whether it is a steroid or a cyclosporine, on the specific drug employed, on the condition being treated and so forth.

Compounds of the invention, i.e. of formulae (I), (II), (IIa), (IIb), (IIc) and (III), have an interesting pharmacokinetic profile and interesting in vitro and in vivo activities.

The invention claimed is:
1. A compound of formula (I)

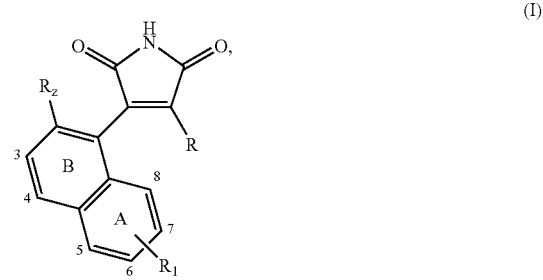

(I)

wherein
$R_1$ is a radical —$(CH_2)_n$—$NR_3R_4$, located on positions 6, 7 or 8,
where
n is 0, 1 or 2; and
each of $R_3$ and $R_4$, independently, is hydrogen; optionally-substituted $C_{1-6}$-alkyl; $C_{3-6}$-cycloalkyl; carboxy-$C_{1-6}$-alkoxy; $C_{2-4}$-alkenyl; or $C_{1-6}$-alkyl-carbonyl; or $R_3$ and $R_4$ form, together with the nitrogen atom to which they are bound, a heterocyclic residue;
$R_2$ is hydrogen; halogen; $CF_3$; OH; CN; SH; $NH_2$; $NO_2$; —CHO; $C(O)NH_2$; optionally-substituted $C_{1-4}$-alkyl; $C_{1-4}$-alkylthio; $C_{1-4}$-alkoxy; $C_{1-4}$-alkyl-sulfoxide; $C_{1-4}$-alkyl-sulfone; $NHC_{1-4}$-alkyl; $N(C_{1-4}$-alkyl$)_2$; $C_{2-4}$-alkenyl; $C_{1-4}$-alkyl-carbamoyl; or $(C_{1-4}$-alkyl$)_2$-carbamoyl;
ring B may further be substituted by a halogen on position 4;
R is a radical of formula (a), (b), (c) or (d),

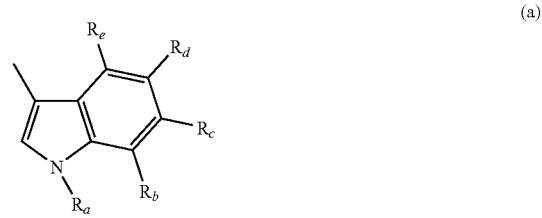

(a)

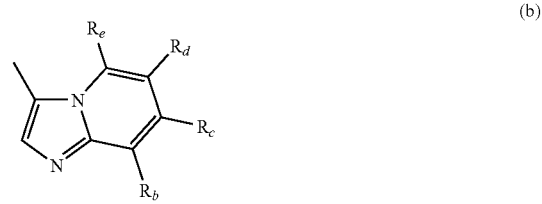

(b)

-continued

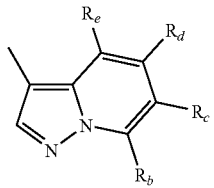
(c)

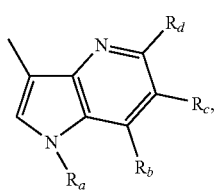
(d)

where
$R_a$ is hydrogen; optionally-substituted $C_{1-6}$-alkyl; $C_{4-8}$-cycloalkyl or an optionally-substituted heterocyclic residue;

each of $R_b$, $R_c$, and $R_d$, independently, is hydrogen; halogen; $CF_3$; CN; optionally-substituted $C_{1-6}$-alkyl; $C_{1-15}$-alkoxy optionally interrupted by one or two oxygen atom(s) and optionally-substituted; carbamoyl-$C_{1-6}$-alkoxy; ($C_{1-4}$-alkyl)carbamoyl-$C_{1-6}$-alkoxy; ($C_{1-4}$-alkyl)$_2$carbamoyl-$C_{1-6}$-alkoxy; carboxy-$C_{1-6}$-alkoxy; or $C_{1-6}$-alkoxy-carbonyl;

or is of the formula O—$(CH_2)_p$—$NR_xR_y$, wherein each of $R_x$ and $R_y$, independently, is hydrogen or $C_{1-4}$-alkyl; and p is 2, 3 or 4;

or is of the formula —$(CH_2)_o$—$NR_vR_w$, wherein each of $R_v$ and $R_w$, independently, is hydrogen; $C_{1-4}$-alkyl$C_{1-6}$-alkoxy;

$C_{1-4}$-alkyl-NH—$C_{1-4}$-alkyl; or $C_{1-4}$-alkyl-N($C_{1-4}$-alkyl)$_2$; and o is 1, 2, 3 or 4;

and $R_e$ is hydrogen; halogen; $CF_3$; CN; $C_{1-6}$-alkyl; or $C_{1-6}$-alkoxy; or $R_a$ and $R_b$ form, together with the

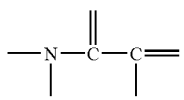

chain to which they are attached, an optionally-substituted heterocyclic residue; and each of $R_c$, $R_d$ and $R_e$, independently, is hydrogen; halogen; $C_{1-6}$-alkyl; or $C_{1-6}$-alkoxy; provided that i) when R is a radical of formula (b), (c) or (d), then $R_1$ is on position 7;

ii) when R is a radical of formula (a), and $R_1$ is on position 6 or position 7; n is 1; $R_2$ is halogen or $C_{1-4}$-alkyl; ring B is not substituted on position 4; and either i) each of $R_3$ and $R_4$, independently, is hydrogen or $C_{1-4}$-alkyl or ii) $R_3$ and $R_4$ form, together with the nitrogen atom to which they are bound, a heterocyclic residue, then at least one of $R_a$, $R_b$, $R_c$, $R_d$ and $R_e$ is other than hydrogen or $C_{1-4}$-alkyl; and/or iii) when $R_1$ is on position 6 and is —$NH_2$; ring B is not substituted on position 4; R is a radical of formula (a); each of $R_2$, $R_3$, $R_4$, $R_b$, $R_c$, $R_d$ and $R_e$ is hydrogen; and $R_a$ is other than hydrogen or $C_{1-4}$-alkyl; or a physiological hydrolysable derivative or salt, thereof.

2. A compound according to claim 1, wherein R is of formula (a), or a physiological hydrolysable derivative or salt, thereof.

3. A compound according to claim 1, wherein R is a radical of formula (a), $R_a$ is hydrogen; optionally-substituted $C_{1-6}$-alkyl; or an optionally-substituted heterocyclic residue; and either each of $R_b$, $R_c$ and $R_d$, independently, is hydrogen; halogen; optionally-substituted $C_{1-6}$-alkyl; $C_{1-15}$-alkoxy optionally interrupted by one or two oxygen atom(s) and optionally-substituted; carbamoyl-$C_{1-6}$-alkoxy; ($C_{1-4}$-alkyl)carbamoyl-$C_{1-6}$-alkoxy; ($C_{1-4}$-alkyl)$_2$carbamoyl-$C_{1-6}$-alkoxy; carboxy-$C_{1-6}$-alkoxy; or $C_{1-6}$-alkoxy-carbonyl; or each of $R_b$, $R_c$ and $R_d$ is of the formula —$(CH_2)_o$—$NHR_v$, where $R_v$ is hydrogen; $C_{1-4}$-alkyl$C_{1-6}$-alkoxy; $C_{1-4}$-alkyl-NH-$C_{1-4}$-alkyl; or $C_{1-4}$-alkyl-N($C_{1-4}$-alkyl)$_2$; and o is 1 or 2; and $R_e$ is hydrogen or $C_{1-4}$-alkyl; or each of $R_b$, $R_c$ and $R_d$ is of formula O—$(CH_2)_p$—$NR_xR_y$, where each of $R_x$ and $R_y$, independently, is hydrogen or $C_{1-4}$alkyl; and p is 2, 3 or 4; and $R_e$ is hydrogen; halogen; $C_{1-6}$-alkyl; or $C_{1-6}$-alkoxy; or $R_a$ and $R_b$ form, together with the

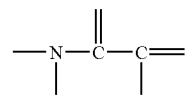

chain to which they are attached, an optionally-substituted heterocyclic residue; and each of $R_c$, $R_d$ and $R_e$, independently, is hydrogen; halogen; $C_{1-6}$-alkyl; or $C_{1-6}$-alkoxy;

or a physiological hydrolysable derivative or salt, thereof.

4. A compound according to claim 1, wherein R is of formula (b), (c) or (d).

5. A compound according to claim 1, in free form or in a pharmaceutically-acceptable salt form, for use as a pharmaceutical.

6. A pharmaceutical composition comprising a compound according to claim 1, in free form or in pharmaceutically-acceptable salt form, in association with a pharmaceutically-acceptable diluent or carrier therefore.

7. A pharmaceutical combination comprising a compound according to claim 1, in free form or in pharmaceutically-acceptable salt for, and a further agent selected from immunosuppressant, immunomodulatory, anti-inflammatory, chemotherapeutic, antiproliferative and anti-diabetic agents.

8. A process for the production of the compound of formula (I) according to claim 1, which process comprises reacting a compound of formula (I')

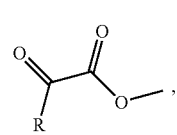
(I')

wherein R is as defined in claim 1,
with a compound of formula (I")

$$R''\text{—}CH_2\text{—}CO\text{—}NH_2 \tag{I''}$$

wherein R" is

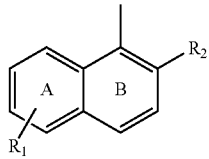

wherein
R₁ and R₂ are as defined in claim 1,
and
ring B may be substituted by an halogen on position meta vis-à-vis R₂, with the provisos (i), (ii) and (iii) as defined in claim 1;
and, where required, converting the resulting compound of formula (I) obtained in free form to a salt form or vice versa, as appropriate.

9. A method for inhibiting T lymphocytes and/or PKC need of such treatment, which comprises administering to said subject an effective amount of a compound according to claim 1, or a pharmaceutically-acceptable salt thereof.

* * * * *